United States Patent [19]

Christensen, IV

[11] Patent Number: 5,643,946

[45] Date of Patent: Jul. 1, 1997

[54] COMPOUNDS USEFUL FOR TREATING ALLERGIC AND INFLAMMATORY DISEASES

[75] Inventor: Siegfried Benjamin Christensen, IV, Philadelphia, Pa.

[73] Assignee: SmithKline Beecham Corporation, Philadelphia, Pa.

[21] Appl. No.: 443,636

[22] Filed: May 18, 1995

Related U.S. Application Data

[63] Continuation of Ser. No. 313,094, filed as PCT/US93/01991, Apr. 2, 1993, Pat. No. 5,552,438, which is a continuation-in-part of Ser. No. 968,762, Oct. 30, 1992, abandoned, which is a continuation-in-part of Ser. No. 862,030, Apr. 2, 1992, abandoned.

[51] Int. Cl.$^6$ .............. A61K 31/115; A61K 31/085; C07C 69/96; C07C 49/355

[52] U.S. Cl. .......... 514/512; 514/362; 514/363; 514/364; 514/381; 514/476; 514/513; 514/521; 514/646; 514/694; 548/127; 548/128; 548/131; 548/134; 548/136; 548/143; 548/252; 560/24; 558/271; 558/426; 562/433

[58] Field of Search .................... 558/426, 271; 548/127, 128, 131, 134, 136, 143, 252; 514/521, 362, 363, 364, 381, 476, 512, 513, 646, 694; 560/24; 562/433

[56] References Cited

U.S. PATENT DOCUMENTS

| | | | |
|---|---|---|---|
| 3,862,239 | 1/1975 | Karmas | 562/469 |
| 4,795,757 | 1/1989 | Regan et al. | 514/415 |

FOREIGN PATENT DOCUMENTS

| | | | |
|---|---|---|---|
| WO/93/07111 | 4/1993 | WIPO | 558/406 |
| WO/93/19720 | 10/1993 | WIPO | 558/406 |
| WO/93/19750 | 10/1993 | WIPO | 558/406 |
| WO/93/19748 | 10/1993 | WIPO | 558/406 |

OTHER PUBLICATIONS

Chemical Abstracts, vol. 90, No. 11, Mar. 1979, abstract 86895p.

*Primary Examiner*—Jacqueline Haley
*Attorney, Agent, or Firm*—James M. Kanagy; Stephen Venetianer; Edward T. Lentz

[57] ABSTRACT

Compounds of the formula

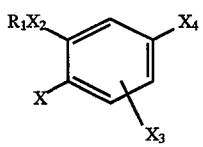

wherein the substituents are as defined herein, are disclosed. Pharmaceutical compositions and methods of treating allergic and inflammatory diseases are also taught.

3 Claims, No Drawings

COMPOUNDS USEFUL FOR TREATING ALLERGIC AND INFLAMMATORY DISEASES

This application is a continuation of U.S. application Ser. No. 08/313,094 filed Sep. 29, 1994, now U.S. Pat. No. 5,552,438; which is a continuation of PCT application PCT/US93/01991 filed 02 Apr. 1993, now abandoned; which is a continuation-in-part of U.S. Ser. No. 07/968,762 filed 30 Oct. 1992, now abandoned; which is a continuation-in-part of U.S. Ser. No. 07/862,030 filed 2 Apr. 1992, now abandoned.

Field of Invention

The present invention relates to novel compounds, pharmaceutical compositions containing these compounds, d their use in treating allergic and inflammatory diseases and for inhibiting the production of Tumor Necrosis Factor (TNF).

BACKGROUND OF THE INVENTION

Bronchial asthma is a complex, multifactorial disease characterized by reversible narrowing of the airway and hyperreactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

One such way is by elevating levels of cAMP (adenosine cyclic 3',5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil alegranulation, and 5) inhibition of monocyte and macrophage activation. Hence, compounds that activate adenvlate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE IV, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barn, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenvlate cyclase activity of target cells is elevated by appropriate hormones or autocoids, as would be the case in vivo. Thus PDE IV inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit the production of Tumor Necrosis Factor (TNF), a serum glycoprotein. Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory. distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), AIDS, ARC (AIDS related complex), keloid formation, scar tissue formation, Crohn's disease. ulceralive colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell-mediated immunity is impaired and infected individuals manifest severe opportunistic infections and/or unusual neoplasms. HIV entry into the T lymphocyte requires T lymphocyte activation. Viruses such as HIV- 1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell-mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the profession of immune dysfunction caused by HIV infection. Monocytes, macrophages, and related cells, such as kupffer and glial cells. have also been implicated in maintenance of the HIV infection. These cells, like T cells, are targets for viral replication and the level of viral replication is dependent upon the activation state of the cells. [See Rosenberg et al., The Immunopathogenesis of HIV Infection, Advances in Immunology, Vol. 57, 1989]. Monokines, such as TNF, have been shown to activate HIV replication in monocytes and/or macrophages [See Poli et al., Proc. Natl. Acad. Sci., 87:782–784, 1990], therefore, inhibition of monokine production or activity aids in limiting HIV profession as stated above for T cells.

TNF has also been implicated in various roles with other viral infections, such as the cytomegalovirus (CMV), influenza virus, adenovirus, and the herpes virus for similar reasons as those noted.

TNF is also associated with yeast and fungal infections. Specifically *Candida albicans* has been shown to induce TNF production in vitro in human monocytes and natural killer cells. [See Riipi et at., Infection and Immunity, 58(9):2750–54, 1990; and Jafari et al., Journal of Infectious Diseases, 164:389–95, 1991. See also Wasan et al., Antimicrobial Agents and Chemotherapy, 35, (10):2046–48, 1991; and Luke et al., Journal of Infectious Diseases, 162:211–214,1990].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

SUMMARY OF THE INVENTION

This invention relates to the novel compounds of the Formula (I), as shown below, useful in the mediation or inhibition of the enzymatic activity (or catalytic activity) of phosphodiesterase IV (PDE IV). The novel compounds of the Formula (I) also have Tumor Necrosis Factor (TNF) inhibitory activity.

This invention also relates to the pharmaceutical compositions comprising a compound of the Formula (I) and a pharmaceutically acceptable carrier or diluent.

The invention also relates to a method of mediation or inhibition of the enzymatic activity (or catalytic activity) of PDE IV in mammals, including humans, which comprises administering to a mammal in need thereof an effective amount of a compound of the Formula (I), as shown below.

The invention further provides a method for the treatment of allergic and inflammatory disease which comprises administering to a mammal, including humans, in need thereof, an effective amount of a compound of the Formula (I).

The invention also provides a method for the treatment of asthma which comprises administering to a mammal, including humans, in need thereof, an effective amount of a compound of the Formula (I).

This invention also relates to a method of inhibiting TNF production in a mammal, including humans, which method comprises administering to a mammal in need of such treatment, an effective TNF inhibiting amount of a compound of the Formula (I). This method may be used for the prophylactic treatment or prevention of certain TNF mediated disease states amenable thereto.

This invention also relates to a method of treating a human afflicted with a human immunodeficiency virus (HIV), which comprises administering to such human an effective TNF inhibiting amount of a compound of the Formula (I).

The compounds of the Formula (I) are also useful in the treatment of additional viral infections, where such viruses are sensitive to upregulation by TNF or will elicit TNF production in vivo.

The compounds of the Formula (I) are also useful in the treatment of yeast and fungal infections, where such yeast and fungi are sensitive to upregulation by TNF or will elicit TNF production in vivo.

The compounds of this invention are represented by Formula (I):

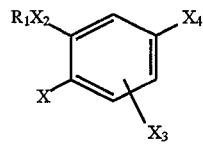

wherein: $R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties may be optionally substituted with one or more halogens;

m is 0 to 2;

n is 1 to 4;

r is 1 to 6;

$R_4$ and $R_5$ are independently selected from hydrogen or a $C_{1-2}$ alkyl;

$R_6$ is hydrogen, methyl, hydroxyl, aryl, halo substituted aryl, aryloxy, aryloxy $C_{1-3}$ alkyl, halo substituted aryloxy $C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group;

provided that:

a) when $R_6$ is hydroxyl, then m is 2; or b) when $R_6$ is hydroxyl, then r is 2 to 6; or c) when $R_6$ is 2-tetrahydropyranyl, 2-tetrahydrothiopyranyl, 2-tetrahydrofuranyl, or 2-tetrahydrothienyl, then m is 1 or 2; or d) when $R_6$ is 2-tetrahydropyranyl, 2-tetrahydrothiopyranyl, 2-tetrahydrofuranyl, or 2-tetrahydrothienyl, then r is 1 to 6;

e) when n is 1 and m is 0, then $R_6$ is other than H in —$(CR_4R_5)_nO(CR_4R_5)_mR_6$;

X is $YR_2$, halogen, nitro, $NR_4R_5$, or formyl amine:

Y is O or $S(O)_{m'}$;

m' is 0, 1, or 2;

$X_2$ is O or $NR_8$;

$X_3$ is hydrogen or X;

$X_4$ is

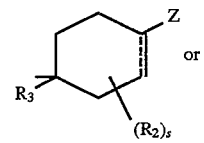

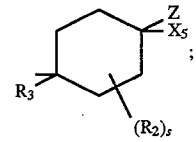

$X_5$ is H, $R_9$, $OR_8$, CN, $C(O)R_8$, $C(O)OR_8$, $C(O)NR_8R_8$, or $NR_8R_8$;

$R_2$ is independently selected from the group consisting of —$CH_3$ and —$CH_2CH_3$ optionally substituted by 1 or more halogens;

s is 0 to 4;

$R_3$ is hydrogen, halogen, $C_{1-4}$ alkyl, $CH_2NHC(O)C(O)NH_2$, halo-substituted $C_{1-4}$ alkyl, —CH=$CR_8'R_8'$, cyclopropyl optionally substituted by $R_8'$, CN, $OR_8$, $CH_2OR_8$, $NR_8R_{10}$, $CH_2NR_8R_{10}$, $C(Z')H$, $C(O)OR_8$, $C(O)NR_8R_{10}$, or C≡$CR_8'$;

Z' is O, $NR_9$, $NOR_8$, NCN, $C(-CN)_2$, $CR_8CN$, $CR_8NO_2$, $CR_8C(O)OR_8$, $CR_8C(O)NR_8R_8$, $C(-CN)NO_2$, $C(-CN)C(O)OR_9$, or $C(-CN)C(O)NR_8R_8$;

Z is $C(Y')R_{14}$, $C(O)OR_{14}$, $C(Y')NR_{10}R_{14}$, $C(NR_{10})NR_{10}R_{14}$, CN, $C(NOR_8)R_{14}$, $C(O)NR_8NR_8C(O)R_8$, $C(O)NR_8NR_{10}R_{14}$, $C(NOR_{14})R_8$, $C(NR_8)NR_{10}R_{14}$, $C(NR_{14})NR_8R_8$, $C(NCN)NR_{10}R_{14}$, $C(NCN)SR_9$, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl); wherein all of the heterocylic ring systems may be optionally substituted one or more times by $R_{14}$;

the dotted line in formula (a) represents a single or double bond;

Y' is O or S;

$R_7$ is $-(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, —F, —Br, —Cl, $-NO_2$, $-NR_{10}R_{11}$, $-C(O)R_8$, $-C(O)OR_8$, $-OR_8$, —CN, $-C(O)NR_{10}R_{11}$, $-OC(O)NR_{10}R_{11}$, $-OC(O)R_8$, $-NR_{10}C(O)NR_{10}R_{11}$, $-NR_{10}C(O)R_{11}$, $-NR_{10}C(O)OR_9$, $-NR_{10}C(O)R_{13}$, $-C(NR_{10})NR_{10}R_{11}$, $-C(NCN)NR_{10}R_{11}$, $-C(NCN)SR_9$, $-NR_{10}C(NCN)SR_9$, $-NR_{10}C(NCN)NR_{10}R_{11}$, $-NR_{10}S(O)_2R_9$, $-S(O)_m'R_9$, $-NR_{10}C(O)C(O)NR_{10}R_{11}$, $-NR_{10}C(O)C(O)R_{10}$, thiazolyl, imidazolyl, oxazolyl, pyrazolyl, triazolyl, or tetrazolyl;

q is 0, 1, or 2;

$R_{12}$ is $C_{3-7}$ cycloalkyl, (2-, 3- or 4-pyridyl), pyrimidyl, pyrazolyl, (1- or 2-imidazolyl), thiazolyl, triazolyl, pyrrolyl, piperazinyl, piperidinyl, morpholinyl, furanyl, (2-or 3-thienyl), (4- or 5-thiazolyl), quinolinyl, naphthyl, or phenyl;

$R_8$ is independently selected from hydrogen or $R_9$;

$R_8'$ is $R_8$ or fluorine;

$R_9$ is $C_{1-4}$ alkyl optionally substituted by one to three fluorines;

$R_{10}$ is $OR_8$ or $R_{11}$;

$R_{11}$ is hydrogen, or $C_{1-4}$ alkyl optionally substituted by one to three fluorines; or when $R_{10}$ and $R_{11}$ are as $NR_{10}R_{11}$ they may together with the nitrogen form a 5 to 7 membered ring optionally containing at least one additional heteroatom selected from O/N/or S:

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_{10}$ and $R_{14}$ are as $NR_{10}R_{14}$ they may together with the nitrogen form a 5 to 7 membered ring optionally containing one or more additional heteroatoms selected from O, N, or S;

provided that:

f) when $R_{12}$ is N-pyrazolyl, N-imidazolyl, N-triazolyl, N-pyrrolyl, N-piperazinyl, N-piperidinyl, or N-morpholinyl, then q is not 1; or g) when $X_2R_1$ is $OCF_2H$ or $OCF_3$, X is F, $OCF_2H$ or $OCF_3$, $X_3$ is H, s is zero, $X_5$ is H, Z is $C(O)OR_{14}$ and $R_{14}$ is $C_{1-7}$ unsubstituted alkyl, then $R_3$ is other than H;

or the pharmaceutically acceptable salts thereof.

DETAILED DESCRIPTION OF THE INVENTION

This invention relates to the novel compounds of Formula (I), and to pharmaceutical compositions comprising a compound of Formula (I) and a pharmaceutically acceptable carrier or diluent. This invention also relates to a method of mediating or inhibiting the enzymatic activity (or catalytic activity) of PDE IV in a mammal in need thereof and to inhibiting the production of TNF in a mammal in need thereof, which comprises administering to said mammal an effective amount of a compound of the Formula (I).

Phosphodiesterase IV inhibitors are useful in the treatment of a variety of allergic and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulceralive colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus, [Kidney Int., 37:362, 1990; Kidney Int., 35:494, 1989] and central nervous system disorders such as depression and multi-infarct dementia.

The compounds of the Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibitors of the Formula (1). Such viruses include, but are not limited to HIV-1, HIV-2 and HIV-3, cytomegalovirus (CMV), influenza, acenovirus and the Herpes group of viruses, such as, but not limited to, *Herpes zoster* and *Herpes simplex*.

This invention more specifically relates to a method of treating a mammal, afflicted with a human immunodeficiency virus (HIV), which comprises administering to such mammal an effective TNF inhibiting amount of a compound of the Formula (I).

The compounds of the Formula (I) may also be used in association with the veterinary treatment of animals, other than in humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anemia virus, caprine arthritis virus, visna virus, maedi virus and other lentiviruses.

The compounds of the Formula (I) are also useful in the treatment of yeast and fungal infections, where such yeas and fungi are sensitive to upregulation by TNF or will elicit TNF production in vivo. A preferred disease state for treatment is fungal meningitis. Additionally, the compounds of the Formula (I) may be administered in conjunction with other drugs of choice for systemic yeast and fungal infections. Drugs of choice for fungal infections, include but are not limited to the class of compounds called the polymixins, such as Polymycin B, the class of compounds called the imidazoles, such as clotrimazole, econazole, miconazole, and ketoconazole; the class of compounds called the triazoles, such as fluconazole, and itranazole, and the class of compound called the Amphotericins, in particular Amphotericin B and liposomal Amphotericin B.

The co-administration of the anti-fungal agent with a compound of the Formula (I) may be in any preferred composition for that compound such as is well known to those skilled in the art, for instance the various Amphotericin B formulations. Co-administration of an anti-fungal agent with a compound of the Formula (I) may mean simultaneous administration or in practice, separate administration of the agents to the mammal but in a consecutive manner. In particular, the compounds of the Formula (I) may be co-administered with a formulation of Amphotericin B, notably for systemic fungal infections. The preferred organism for treatment is the Candida organism. The compounds of the Formula (I) may be co-administered in a similar manner with anti-viral or anti-bacterial agents.

The compounds of the Formula (I) may also be used for inhibiting and/or reducing the toxicity of an anti-fungal, anti-bacterial or anti-viral agent by administering an effective amount of a compound of the Formula (I) to a mammal in need of such treatment. Preferably, a compound of the Formula (I) is administered for inhibiting or reducing the toxicity of the Amphotericin class of compounds, in particular Amphotericin B.

When $R_1$ for the compounds of the Formula (I) is an alkyl substituted by 1 or more halogens, the halogens are preferably fluorine and chlorine, more preferably a $C_{1-4}$ alkyl substituted by 1 or more fluorines. The preferred halo-substituted alkyl chain length is one or two carbons, and most preferred are the moieties —$CF_3$, —$CH_2F$, —$CHF_2$, —$CF_2CHF_2$, —$CH_2CF_3$, and —$CH_2CHF_2$. Preferred $R_1$ substituents for the compounds of the Formula (I) are $CH_2$-cyclopropyl, $CH_2$—$C_{5-6}$ cycloalkyl, $C_{4-6}$ cycloalkyl, $C_{7-11}$ polycycloalkyl, (3- or 4-cyclopentenyl), phenyl, tetrahydrofuran-3-yl, benzyl or $C_{1-2}$ alkyl optionally substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4}OH$.

When the $R_1$ term contains the moiety $(CR_4R_5)$, the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be —$CH_2CH$(—$CH_3$)—, for instance. The individual hydrogen atoms of the repeating methylene unit or the branching hydrocarbon can optionally be substituted by fluorine independent of each other to yield, for instance, the preferred $R_1$ substitutions, as noted above.

When $R_1$ is a $C_{7-11}$ polycycloalkyl, examples are bicyclo [2.2.1]-heptyl, bicyclo[2.2.21]octyl, bicyclo[3.2.1]octyl, tricyclo[5.2.1.0$^{2,6}$]decyl, etc. additional examples of which are described in Saccamano et al., WO 87/06576, published 5 November 1987, whose disclosure is incorporated herein by reference in its entirety.

Z is preferably $C(O)R_8$, $C(O)OR_8$, $C(O)NR_8R_8$, $C(NR_8)NR_8R_8$, CN, $C(NOR_8)R_8$, $C(O)NR_8NR_8C(O)R_8$, $C(NR_8)NR_8R_8$, $C(NCN)NR_8R_8$, $C(NCN)SR_9$, (1-, 4- or 5-{$R_8$}-2-imidazolyl), (1-, 4- or 5- {$R_8$}-3-pyrazol), (1-, 2- or 5-{$R_8$}-4-triazolyl[1,2,3]), (1-, 2-, 4- or 5-{$R_8$}-3-triazolyl[1,2,4]), (1- or 2-{$R_8$}-5-tetrazolyl), (4- or 5-{$R_8$}-2-oxazolyl, (3- or 4-{$R_8$}-5-isoxazolyl), (3-{$R_8$}-5-oxadiazolyl[1,2,4]), (5-{$R_8$}-3-oxadiazolyl[1,2,4]), (5-{$R_8$}-2-oxadiazolyl[1,3,4]), (5- {$R_8$}-2-thiadiazolyl[1,3,4]), (4- or 5-{$R_8$}-2-thiazolyl), (4- or 5- {$R_8$}-2-oxazolidinyl), (4- or 5- {$R_8$}-2-thiazolidinyl),( 1-, 4- or 5-{$R_8$}-2-imidazolidinyl); most preferred are those compounds wherein the $R_8$ group of Z is $R_4$.

$X_5$ is preferably hydrogen, $C_{1-2}$ alkyl optionally substituted by one to three fluorines, $OR_8$, CN, $C(O)R_8$, $C(O)OR_8$, $C(O)NR_8R_8$, or $NR_8R_8$.

Preferred X groups for Formula (I) are those wherein X is $YR_2$ and Y is oxygen. The preferred $X_2$ group for Formula (I) is that wherein $X_2$ is oxygen. The preferred $X_3$ group for Formula (I) is that wherein $X_3$ is hydrogen. Preferred $R_2$ groups, where applicable, are $C_{1-2}$ alkyl optionally substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

Preferred $R_3$ moieties are $C(O)NH_2$, $C\equiv CR_8$, CN, $C(Z')$ H, $CH_2OH$, $CH_2F$, $CF_2H$, and $CF_3$. More preferred are $C\equiv CH$ and CN. Z' is preferably O or $NOR_8$.

Preferred $R_7$ moieties include optionally substituted —$(CH_2)_{1-2}$(cyclopropyl), —$(CH_2)_{0-2}$(cyclobutyl),—$(CH_2)_{0-2}$(cyclopentyl), —$(CH_2)_{0-2}$(cyclohexyl), —$(CH_2)_{0-2}$(2-, 3- or 4-pyridyl), —$(CH_2)_{1-2}$(2-imidazolyl), —$(CH_2)_2$(4-morpholinyl), —$(CH_2)_2$(4-piperazinyl), —$(CH_2)_{1-2}$(2-thienyl), —$(CH_2)_{1-2}$(4-thiazolyl), and —$(CH_2)_{0-2}$phenyl;

Preferred rings when $R_{10}$ and $R_{11}$ in the moiety —$NR_{10}R_{11}$ together with the nitrogen to which they are attached form a 5 to 7 membered ring optionally containing at least one additional heteroatom selected from O/N/or S include, but are not limited to 1-imidazolyl, 2—($R_8$)-1-imidazolyl, 1-pyrazolyl, 3-($R_8$)- 1-pyrazolyl, 1-triazolyl, 2-triazolyl, 5-($R_8$)-1-triazolyl, 5-($R_8$)-2-triazolyl, 5-($R_8$)-1-tetrazolyl, 5-($R_8$)-2-tetrazolyl, 1-tetrazolyl, 2-tetrazolyl, morpholinyl, piperazinyl, 4-($R_8$)-1-piperazinyl, or pyrrolyl ring.

Preferred rings when $R_{10}$ and $R_{14}$ in the moiety —$NR_{10}R_{14}$ together with the nitrogen to which they are attached may form a 5 to 7 membered ring optionally containing at least one additional heteroatom selected from O, N, or S include, but are not limited to 1-imidazolyl, 1-pyrazolyl, 1-triazolyl, 2-triazolyl, 1-tetrazolyl, 2-tetrazolyl, morpholinyl, piperazinyl, and pyrrolyl. The respective rings may be additionally substituted, where applicable, on an available nitrogen or carbon by the moiety $R_7$ as described herein for Formula (I). Illustrations of such carbon substitutions includes, but are not limited to, 2-($R_7$) -1-imidazolyl, 4-($R_7$)-1-imidazolyl, 5-($R_7$)-1-imidazolyl, 3-($R_7$)-1-pyrazolyl, 4-($R_7$)-1-pyrazolyl, 5-($R_7$)-1-pyrazolyl, 4-($R_7$)-2-triazolyl, 5-($R_7$)-2-triazolyl, 4-($R_7$)-1-triazolyl, 5-($R_7$)-1-tetrazolyl, and 5-($R_7$)-2-tetrazolyl. Applicable nitrogen substitution by $R_7$ includes, but is not limited to, 1-($R_7$)-2-tetrazolyl, 2-($R_7$)-1-tetrazolyl, 4-13 ($R_7$)-1-piperazinyl. Where applicable, the ring may be substituted one or more times by $R_7$.

Preferred groups for $NR_{10}R_{14}$ which contain a heterocyclic ring are 5-($R_{14}$)-1-tetrazolyl, 2-($R_{14}$)-1-imidazolyl, 5-($R_{14}$)-2-tetrazolyl, or 4-($R_{14}$)-1-piperazinyl.

Preferred rings for $R_{13}$ include (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2,4-, or 5-imidazolidinyl).

When the $R_7$ group is optionally substituted by a heterocyclic ring such as imidazolyl, pyrazolyl, triazolyl, tetrazolyl, or thiazolyl, the heterocyclic ring itself may be optionally substituted by $R_8$ either on an available nitrogen or carbon atom, such as 1-($R_8$)-2-imidazolyl, 1-($R_8$)-4-imidazolyl, 1-($R_8$)-5-imidazolyl, 1-($R_8$)-3-pyrazolyl, 1-($R_8$)-4-pyrazolyl, 1-($R_8$)-5-pyrazolyl, 1-($R_8$)-4-triazolyl, or 1-($R_8$)-5-triazolyl. Where applicable, the ring may be substituted one or more times by $R_8$.

Preferred are those compounds of the Formula (I) wherein $R_1$ is —$CH_2$-cyclopropyl, —$CH_2$—$C_{5-6}$ cycloalkyl, —$C_{4-6}$ cycloalkyl, tetrahydrofuran-3-yl, (3- or 4-cyclopentenyl), benzyl or —$C_{1-2}$ alkyl optionally substituted by 1 or more fluorines, and —$(CH_2)_{2-4}$ OH; $R_2$ is methyl or fluoro-substituted alkyl, $R_3$ is CN or C≡$CR_8$; and X is $YR_2$.

Most preferred are those compounds wherein $R_1$ is —$CH_2$-cyclopropyl, cyclopentyl, methyl or $CF_2H$; $R_3$ is CN or C≡CH; X is $YR_2$; Y is oxygen; $X_2$ is oxygen; $X_3$ is hydrogen; and $R_2$ is $CF_2H$ or methyl.

A preferred subgenus of the compounds of the Formula (I) is the compounds of the Formula (Ia)

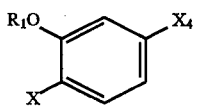

wherein:

$R_1$ is $CH_2$-cyclopropyl, $CH_2$—$C_{5-6}$ cycloalkyl, $C_{4-6}$ cycloalkyl, $C_{7-11}$ polycycloalkyl, (3- or 4-cyclopentenyl), phenyl, tetrahydrofuran-3-yl, benzyl or $C_{1-2}$ alkyl optionally substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4}OH$;

X is $YR_2$, halogen, nitro, $NR_4R_5$, or formyl amine;

$X_4$ is

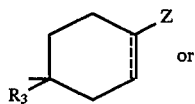

or

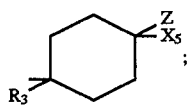

$X_5$ is H, $R_9$, $OR_8$, CN, C(O)$R_8$, C(O)O$R_8$, C(O)$NR_8R_8$, or $NR_8R_8$;

Y is O or S(O)$_{m'}$;

m' is 0, 1, or 2;

$R_2$ is —$CH_3$ or —$CH_2CH_3$ optionally substituted by 1 or more halogens;

$R_3$ is hydrogen, $C_{1-4}$ alkyl, $CH_2NHC(O)C(O)NH_2$, halo-substituted $C_{1-4}$ alkyl, CN, $CH_2OR_8$, C(Z')H, C(O)O$R_8$, C(O)$NR_8R_{10}$, or C≡$CR_8$;

Z' is O or $NOR_8$;

Z is C(O)$R_{14}$, C(O)O$R_{14}$, C(O)$NR_{10}R_{14}$, C($NR_{10}$)$NR_{10}R_{14}$, CN, C(NO$R_8$)$R_{14}$, C(O)$NR_8NR_8C(O)R_8$, C(O)$NR_8NR_{10}R_{14}$, C(NO$R_{14}$)$R_8$, C($NR_8$)$NR_{10}R_{14}$, C($NR_{14}$)$NR_8R_8$, C(NCN)$NR_{10}R_{14}$, C(NCN)S$R_9$, (1-, 4- or 5-{$R_{14}$}-2-imidazolyl), (1-, 4- or 5-{$R_{14}$}-3-pyrazolyl), (1-, 2- or 5-{$R_{14}$-}-4-triazolyl[1,2,3]), (1-, 2-, 4- or 5-{$R_{14}$-}-3-triazolyl[1,2,4]), (1- or 2-{$R_{14}$-}-5-tetrazolyl), (4- or 5-{$R_{14}$}-2-oxazolyl), (3- or 4-{$R_{14}$}-5-isoxazolyl), (3-{$R_{14}$-}-5-oxadiazolyl[1,2,4]), (5-{$R_{14}$}-3-oxadiazolyl[1,2,4]), (5-{$R_{14}$-}-2-oxadiazolyl[1,3,4]), (5-{$R_{14}$}-2-thiadiazolyl[1,3,4]), (4- or 5-{$R_{14}$}-2-thiazolyl), (4- or 5-{$R_{14}$}-2-oxazolidinyl), (4- or 5-{$R_{14}$}-2-thiazolidinyl), (1-, 4- or 5-{$R_{14}$}-2-imidazolidinyl);

$R_7$ is —$(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, —F, —Br, —Cl, —$NO_2$, —$NR_{10}R_{11}$, —C(O)$R_8$, —C(O)O$R_8$, —O$R_8$, —CN, —C(O)$NR_{10}R_{11}$, —OC(O)$NR_{10}R_{11}$, —OC(O)$R_8$, —$NR_{10}$C(O)$NR_{10}R_{11}$, —$NR_{10}$C(O)$R_{11}$, —$NR_{10}$C(O)O$R_9$, —$NR_{10}$C(O)$R_{13}$, —C($NR_{10}$)$NR_{10}R_{11}$, —C(NCN)$NR_{10}R_{11}$, —C(NCN)S$R_9$, —$NR_{10}$C(NCN)S$R_9$, —$NR_{10}$C(NCN)$NR_{10}R_{11}$, —$NR_{10}S(O)_2R_9$, —S(O)$_{m'}R_9$, —$NR_{10}$C(O)C(O)$NR_{10}R_{11}$, —$NR_{10}$C(O)C(O)$R_{10}$, thiazolyl, imidazolyl, oxazolyl, pyrazolyl, triazolyl, or tetrazolyl;

q is 0, 1, or 2;

$R_{12}$ is $C_3$–$C_7$ cycloalkyl, (2-, 3- or 4-pyridyl), (1- or 2-imidazolyl), piperazinyl, morpholinyl, (2- or 3-thienyl), (4- or 5-thiazolyl), or phenyl;

the dotted line formula (a) represents a single or double bond:

$R_8$ is independently selected from hydrogen or $R_9$;

$R_9$ is $C_{1-4}$ alkyl optionally substituted by one to three fluorines;

$R_{10}$ is O$R_8$ or $R_{11}$;

$R_{11}$ is hydrogen or $C_{1-4}$ alkyl optionally substituted by one to three fluorines; or when $R_{10}$ and $R_{11}$ are as $NR_{10}R_{11}$ they may together with the nitrogen form a 5 to 7 membered ring optionally containing at least one additional heteroatom selected from O/N/or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_{10}$ and $R_{14}$ are as $NR_{10}R_{14}$ they may together with the nitrogen form a 5 to 7 membered ring optionally containing one or more additional heteroatoms selected from O/N/or S;

provided that:
a) when $R_{12}$ is N-imidazolyl, N-triazolyl, N-pyrrolyl, N-piperazinyl, or N-morpholinyl, then q is not 1; or
b) when $R_1$ is $CF_2H$ or $CF_3$, X is F, O$CF_2H$, or O$CF_3$, $X_5$ is H, Z is C(O)O$R_{14}$ and $R_{14}$ is $C_{1-7}$ unsubstituted alkyl, then $R_3$ is other than H;

or the pharmaceutically acceptable salts thereof.

Exemplified compounds of Formula (I) are:

methyl 4-cyano-4-(3-cyclopentyloxy-4-methoxyphenyl)cyclohex-1-ene-1-carboxylate;

4-cyano-4-(3-cyclopentyloxy-4-methoxyphenyl)cyclohex-1-ene-1-carboxylic acid;

methyl cis-[4-cyano-4-(3-cyclopentyloxy-4-methoxyphenyl)cyclohexane-1-carboxylate];

methyl trans-[4-cyano-4-(3-cyclopentyloxy-4-methoxyphenyl)cyclohexane-1-carboxylate];

methyl cis- [4-(3,4-bisdifluoromethoxyphenyl)-4-cyanocyclohexane-1-carboxylate];

methyl trans-[4-(3,4-bisdifluoromethoxyphenyl)-4-cyanocyclohexane-1-carboxylate];

cis-[4-cyano-4-(3-cyclopentyloxy-4-methoxyphenyl)cyclohexane-1-carboxylic acid];

cis-[4-cyano-4-(3-cyclopentyloxy-4-methoxyphenyl)cyclohexane-1-carboxylate], tris(hydroxymethyl) ammonium methane salt;

cis-[4-(3,4-bisdifluoromethoxyphenyl)-4-cyanocyclohexane-1-carboxylic acid];

trans-[4-cyano-4-(3-cyclopentyloxy-4-methoxyphenyl) cyclohexane-1-carboxylic acid];

cis-[4-cyano-4-(3-cyclopropylmethoxy-4-methoxyphenyl)cyclohexane-1-carboxylic acid]:

trans-[4-cyano-4-(3-cyclopropylmethoxy-4-methoxyphenyl)cyclohexane-1- carboxylic acid];

methyl cis-[4-cyano-4-(3-cyclopropylmethoxy-4-methoxyphenyl)cyclohexane-1-carboxylate];

methyl trans-[4-cyano-4-(3-cyclopropylmethoxy-4-methoxyphenyl)cyclohexane-1-carboxylate];

methyl cis-[4-cyano-4-(3-cyclopropylmethoxy-4-difluoromethoxyphenyl)cyclohexane-1-carboxylate];

methyl trans-[4-cyano-4-(3-cyclopropylmethoxy-4-difluoromethoxyphenyl)cyclohexane-1-carboxylate];

cis-[4-cyano-4-(3-cyclopropylmethoxy-4-difluoromethoxyphenyl )cyclohexane-1-carboxylic acid];

trans-[4-cyano-4-(3-cyclopropylmethoxy-4-difluoromethoxyphenyl)cyclohexane, 1-carboxylic acid];

cis-[4-cyano-4-(3-cyclopentyloxy-4-methoxyphenyl) cyclohexane-1-carboxamide];

cis-[4-cyano-4-(3,4-bisdifluoromethoxyphenyl) cyclohexane-1-carboxamide];

trans-[4-cyano-4-(3,4-bisdifluoromethoxyphenyl) cyclohexane-1-carboxamide];

cis-[4-cyano-4-(3,4-bisdifluoromethoxyphenyl) cyclohexane-1-carbohydrazide];

cis-[4-cyano-4-(3,4-bisdifluoromethoxyphenyl) cyclohexane-1-(2-acetylcarbohydrazide)];

cis-{4-(3,4-bisdifluoromethoxyphenyl)-4-cyano-1-(3-methyl[1,2,4]oxadiazol-5-yl)cyclohexane};

cis-{4-(3,4-bisdifluoromethoxyphenyl)-4-cyano-1-(2-methyl[1,3,4]oxadiazol-5-yl)cyclohexane};

cis-{4-(3,4-bisdifluoromethoxyphenyl)-4-cyano 1-(2-methyl[1,3,4]thiadiazol-5-yl)cyclohexane};

cis-[4-cyano-4-(3-cyclopropylmethoxy-4-methoxyphenyl)-1-hydroxy-1-tris(methylthio) methylcyclohexane];

methyl cis-[4-cyano-4-(3-cyclopropylmethoxy-4-methoxyphenyl)-1-hydroxy-cyclohexane-1-carboxylate];

cis-[4-cyano-4-(3-cyclopropylmethoxy-4-methoxyphenyl)-1-hydroxycyclohexane-1-carboxylic acid];

cis-[4-cyano-4-(3-cyclopropylmethoxy-4-methoxyphenyl)-1-hydroxycyclohexane-1-carboxamide];

methyl cis-[4-cyano-4-(3-cyclopropylmethoxy-4-methoxyphenyl)-1-methoxycyclohexane-1-carboxylate];

cis-[4-cyano-4-(3-cyclopropylmethoxy-4-methoxyphenyl)-1-methoxycyclohexane-1-carboxylic acid];

cis-[4-cyano-4-(3-cyclopropylmethoxy-4-methoxyphenyl)-1-methoxycyclohexane-1-carboxamide];

trans-[4-cyano-4-(3-cyclopropylmethoxy-4-methoxyphenyl)-1-hydroxy-cyclohexane-1-carboxaldehyde];

methyl trans-[4-cyano-4-(3-cyclopropylmethoxy-4-methoxyphenyl)-1-hydroxycyclohexane-1-carboxylate];

trans-[4-cyano-4-(3-cyclopropylmethoxy-4-methoxyphenyl)-1-hydroxycyclohexane-1-carboxylic acid];

methyl trans-[4-cyano-4-(3-cyclopropylmethoxy-4-methoxyphenyl )-1-methoxycyclohexane-1-carboxylate];

trans-[4-cyano-4-(3-cyclopropylmethoxy-4methoxyphenyl)-1-methoxycyclohexane-1-carboxylic acid];

trans-[4-cyano-4-(3-cyclopropylmethoxy-4-methoxyphenyl)-1-methoxycyclohexane-1-carboxamide];

cis-[4-cyano-4-(3-cyclopentyloxy-4-methoxyphenyl) cyclohexane-1-carboxamic acid];

N-methyl-cis-[4-cyano-4-(3-cyclopentyloxy-4-methoxyphenyl)cyclohexane-1-carboxamic acid];

cis-[4-cyano-4-(3-cyclopentyloxy-4-methoxyphenyl) cyclohexane-1-N-(2-cyanoethyl)carboxamide];

cis-[1-(2-cyanoethyl)-5-{4-cyano-4-(3-cyclopentyloxy-4-methoxyphenyl)cyclohexyl}tetrazole]; and cis-[4-cyano-4-(3-cyclopentyloxy-4-methoxyphenyl)-1-(tetrazol-5-yl)cyclohexane].

Some compounds of Formula (I) may exist in both racemic and optically active forms; some may also exist in distinct diastereomeric forms possessing distinct physical and biological properties. All of these compounds are considered to be within the scope of the present invention. Therefore another aspect of the present invention is the administration of either a racemate, a single enantiomeric form, a single diastereomeric form, or mixtures thereof.

The terms cis and trans denote stereochemistry at the C-1 position of the cyclohexane ring relative to the $R_3$ group at the C-4 position.

The terms "$C_{1-3}$ alkyl", "$C_{1-4}$ alkyl", "$C_{1-6}$ alkyl" or "alkyl" include both straight or branched chain radicals of 1 to 10, unless the chain length is limited thereto, including, but not limited to methyl, ethyl, n-propyl, isopropyl, n-butyl, sec-butyl, isobutyl, tert-butyl, and the like. "Alkenyl" includes both straight or branched chain radicals of 1 to 6 carbon lengths, unless the chain length is limited thereto, including but not limited to vinyl, 1-propenyl, 2-propenyl, 2-propynyl, or 3-methyl-2-propenyl. "Cycloalkyl" or "cycloalkyl alkyl" includes groups of 3–7 carbon atoms, such as cyclopropyl, cyclopropylmethyl, cyclopentyl, or cyclohexyl. "Aryl" or "aralkyl", unless specified otherwise, means an aromatic ring or ring system of 6–10 carbon atoms, such as phenyl, benzyl, phenethyl, or naphthyl. Preferably the aryl is monocyclic, i.e, phenyl. The alkyl chain includes both straight or branched chain radicals of 1 to 4 carbon atoms. "Heteroaryl" as used herein is meant an aromatic ring system containing one or more heteroatoms, such as imidazolyl, triazolyl, oxazolyl, pyridyl, pyrimidyl, pyrazolyl, pyrrolyl, furanyl, or thienyl. "Halo" as used herein is meant all halogens, i.e., chloro, fluoro, bromo, or iodo.

The phrase "inhibiting the production of IL-1" or "inhibiting the production of TNF" means:

a) a decrease of excessive in vivo IL-1 or TNF levels, respectively, in a human to normal levels or below normal levels by inhibition of the in vivo release of IL-1 by all cells, including but not limited to monocytes or macrophages;

b) a down regulation, at the translational or transcriptional level, of excessive in vivo IL-1 or TNF levels, respectively, in a human to normal levels or below normal levels; or c) a down regulation, by inhibition of the direct synthesis of IL-1 or TNF levels as a postranslational event.

"TNF mediated disease or disease states" means any and all disease states in which TNF plays a role, either by production of TNF itself, or by TNF causing another cytokine to be released, such as but not limited to IL-1 or IL-6. A disease state in which IL-1, for instance is a major component, and whose production or action, is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise. Preferably TNF-α is inhibited.

"Cytokine" means any secreted polypeptide that affects the functions of cells, and is a molecule which modulates interactions between cells in immune, inflammatory, or hematopoietic responses. A cytokine includes, but is not limited to, monokines and lymphokines regardless of which cells produce them. For instance, a monokine is generally referred to as being produced and secreted by a mononuclear cell, such as a macrophage and/or monocyte, but many other cells produce monokines, such as natural killer cells, fibroblasts, basophils, neutrophils, endothelial cells, brain astrocytes, bone marrow stromal cells, epidermal keratinocytes, and B-lymphocytes. Lymphokines are generally referred to as being produced by lymphocyte cells. Examples of cytokines for the present invention include, but are not limited to, Interleukin-1 (IL-1), Interleukin-6 (IL-6), Interleukin-8 (IL-8), Tumor Necrosis Factor-alpha (TNF-α) and Tumor Necrosis Factor-beta (TNF-β).

The cytokine inhibited by the present invention for use in the treatment of a HIV-infected human must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration. Preferably this cytokine is TNF-α.

All of the compounds of Formula (I) are useful in the method of inhibiting the production of TNF, preferably by macrophages, monocytes or macrophages and monocytes, in a mammal, including humans, in need thereof. All of the compounds of Formula (I) are useful in the method of inhibiting or mediating the enzymatic or catalytic activity of PDE IV and in treatment of disease states mediated thereby.

METHODS OF PREPARATION:

Preparing compounds of the Formula (I) can be carried out by one of skill in the art according to the procedures outlined in the Examples, infra. The preparation of any remaining compounds of the Formula (I) not described therein may be prepared by the analogous processes disclosed herein which comprise:

a) for compounds of the Formula (I) wherein $R_3$ is H, CN, $OR_9$, $C_{1-4}$ alkyl or $C_{1-4}$ halosubstituted alkyl, wherein X or $X_3$ is other than Br, I, $NO_2$, amino, formyl amine or S(O)m' when m' is 1 or 2, wherein Z is CHO and the double bond is present, reacting a compound of the Formula (2)

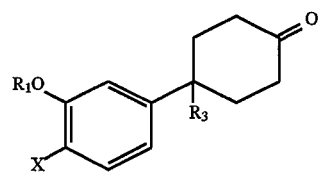

wherein $R_1$ represents $R_1$ as defined in relation to Formula (I) or a group convertable to $R_1$ and X and $X_3$ represent X and $X_3$ as defined in relation to Formula (I) or a group convertable to X or $X_3$ and $R_3$ represents $R_3$ as defined in relation to Formula (I) or a group convertable to $R_3$, with nitromethane in a suitable non-reacting solvent in the presence of a base (catalyst) to provide compounds of the Formula (I) wherein $R_3$ is H, CN, $OR_9$, $C_{1-4}$ alkyl or $C_{1-4}$ halosubstituted alkyl, wherein X and $X_3$ are other than Br, I, $NO_2$, amino, formyl amine or S(O)m' when m' is 1 or 2, wherein Z is $CH_2NO_2$ and the double bond is present; treatment of such compounds with a base, such as sodium methoxide, in the presence of. e.g., buffered titanium trichloride, provides compounds of the Formula (I) wherein $R_3$ is H, CN, $OR_9$, $C_{1-4}$ alkyl or $C_{1-4}$ halosubstituted alkyl, wherein X or $X_3$ are other than Br, I, $NO_2$, amino, formyl amine or S(O)m' when m' is 1 or 2 and wherein Z is CHO and the double bond is present. Double bond reduction of such compounds of the Formula (I) provides the corresponding saturated ring Formula (I) compounds; oxidation of the aldehyde function of either these saturated or unsaturated compounds of the Formula (I) provides the corresponding Formula (I) carboxylates (Z=COOH), which may be converted by standard procedures with proper manipulation of any chemically sensitive functional groups to the corresponding ester, amide, nitrile, oxazolidinone, etc., Z groups of the Formula (I).

Alternatively, reaction of a compound of the Formula (2) with, e.g., tosylmethyl isocyanide and potassium t-butoxide (followed by hydrolysis) or lithium methoxyphenylthiotrimethylsilylmethane (followed by hydrolysis) provides compounds of the Formula (I) wherein $R_3$ is H, CN, $OR_9$, $C_{1-4}$ alkyl or $C_{1-4}$ halosubstituted alkyl, wherein X and $X_3$ are other than Br, I, $NO_2$, amino, formyl amine or S(O)m' when m' is 1 or 2, wherein Z is $CO_2R_{15}$, the double bond is present, and $R_{15}$ is H or simple alkyl; these then may be converted by standard procedures with proper manipulation (protection/deprotection) of any chemically sensitive functional groups to the corresponding ester, amide, nitrile, oxazolidinone, etc., Z groups of the Formula (I).

Alternatively, reaction of a compound of the Formula (2) with, e.g., triflic anhydride in the presence of an appropriate tertiary amine base, or with an alkyl lithium at a reduced temperature followed by treatment with N-phenyl trifluorosulfonimide, provides the corresponding enol triflate, which is then reacted with carbon monoxide in the presence of an alcohol or amine and an appropriate palladium catalyst to provide compounds of the Formula (I) wherein $R_3$ is H, CN, $OR_9$, $C_{1-4}$ alkyl or $C_{1-4}$ halosubstituted alkyl, wherein X and $X_3$ are other than Br, I, $NO_2$, amino, formyl amine or S(O)m' when m' is 1 or 2, wherein Z is $CO_2R_{15}$ or $CONR_{10}R_{14}$, the double bond is present, and $R_{15}$ is H or simple alkyl; these then may be convened by standard procedures with proper manipulation (protection/deprotection) of any chemically sensitive functional groups to the corresponding ester, amide, nitrile, oxazolidinone, etc., Z groups of the Formula (I).

Alternatively, reaction of a compound of the Formula (2) with, e.g., lithium tris(methylthio)$_m$ethane at reduced temperature, followed by mercury salt hydrolysis and alcohol treatment provides compounds of the Formula (I) wherein $R_3$ is H, CN, $OR_9$, $C_{1-4}$ alkyl or $C_{1-4}$ halosubstituted alkyl, wherein X and $X_3$ are other than Br, I, $NO_2$, amino, formyl amine or S(O)m' when m' is 1 or 2, wherein Z is $CO_2R_{15}$ and $X_5$ is OH, the double bond is absent, and $R_{15}$ is H or simple alkyl. Such compounds may also be obtained by reaction of a compound of the Formula (2) with trimethylsulfoxonium iodide or trimethylsulfonium iodide and an appropriate base, such as sodium hydride, to provide the exo-epoxide followed by treatment with aqueous potassium hydroxide in, e.g., dimethylsulfoxide and oxidation of the resulting primary alcohol to the carboxyl provides compounds of the Formula (I) wherein $R_3$ is H, CN, $OR_9$, $C_{1-4}$ alkyl or $C_{1-4}$ halosubstituted alkyl, wherein X and $X_3$ are other than Br, I, $NO_2$, amino, formyl amine or S(O)m' when m' is 1 or 2, wherein Z is $CO_2R_{15}$ and $X_5$ is OH, the double bond is absent, and $R_{15}$ is H or simple alkyl; the $R_5$ hydroxyl may be alkylated and these compounds then may be convened by standard procedures with proper manipulation (protection/deprotection) of any chemically sensitive functional groups to the corresponding ester, amide, nitrile, oxazolidinone, etc., Z groups of the Formula (I).

Alternatively, reaction of a compound of the Formula (2) with, e.g., 2-lithio-2-(trimethylsilyl)-1,3-dithiane followed by acidic hydrolysis with a mercury salt, such as mercury (II) chloride, or reaction of a compound of the Formula (2) with, e.g., sodio-[diethyl t-butoxy(cyano)methyl phosphonate] followed by treatment with acetic anhydride and a zinc halide and then followed by treatment with an alkoxide provides compounds of the Formula (I) wherein $R_3$ is H, CN, $OR_9$, $C_{1-4}$ alkyl or $C_{1-4}$ halosubstituted alkyl, wherein X and $X_3$ are other than Br, I, $NO_2$, amino, formyl amine or S(O)m' when m' is 1 or 2, wherein Z is $CO_2R_{15}$, the double bond is not present, and $R_{15}$ is H or simple alkyl and $R_5$ is H; these then may be convened by standard procedures with proper manipulation (protection/deprotection) of any chemically sensitive functional groups to the corresponding ester, amide, nitrile, oxazolidinone, etc., Z groups of the Formula (I).

Preparation of such compounds of the Formula (I) wherein $R_3$ is C(=Z')H proceed in an analogous fashion from the compound of the Formula (2) wherein =Z' is an aldehyde protecting group, such as a dimethylacetal or a dioxolane, followed by aldehyde deprotection and subsequent manipulation by standard procedures known to those of skill in the art to the remaining compounds of the Formula (I) wherein Z' is other than O or $R_3$ is other than H, CN, $OR_9$, $C_{1-4}$ alkyl or $C_{1-4}$ halosubstituted alkyl.

With proper manipulation (protection/deprotection) of any chemically sensitive functional groups:

a) Compounds of the Formula (I) wherein X or $X_3$ are formyl amine may be formed at the last step, by formylating a compound wherein X or $X_3$ is $NH_2$, obtained by removal of a protecting group from the amine functionality; such protective groups are well known to those skilled in the art, See Greene, T. and Wuts, P. G. M., Protecting Groups in Organic Synthesis, 2nd Ed., John Wiley and Sons, New York (1991).

c) Compounds of the Formula (I) wherein X or $X_3$ are Br or I may be prepared from a similarly deprotected amine by diazotization of the amine and diazonium displacement.

d) Compounds of the Formula (I) wherein X or $X_3$ are $NO_2$ may be prepared from a similarly deprotected amine by oxidation of the amine to the nitro group.

e) Compounds of the Formula (I) wherein Y is S(O)m' when m' is 1 or 2 may be prepared from the compounds of the Formula (I) wherein Y is S by oxidation of the $SR_2$ moiety under conditions well known those skilled in the art Compounds of the Formula (2) may be prepared in turn by the processes described in co-pending application U.S. Ser. No. 07/862,083 filed 2 Apr. 1992 and the corresponding continuation-in-part application filed on even date herewith.

It will be recognized that compounds of the Formula (I) may exist in two distinct diastereomeric forms possessing distinct physical and biological properties; such isomers may be separated by standard chromatographic methods.

The following examples and methods are provided to illustrate how the make and use the invention. These materials are not intended to limit the invention in any manner; please refer to the claims appended hereto for determining what has been reserved to the inventors hereunder.

SYNTHETIC EXAMPLES

EXAMPLE 1

Methyl 4-cyano-4-(3-cyclopentyloxy-4-methoxyphenyl)cyclohex-1-ene-1-carboxylate 4-Cyano-4-(3-cyclopentyloxy-4-methoxyphenyl)-1-cyclohexenyl trifluoromethylsulfonyl To a solution of diisopropylamine [1.95 milliliters (hereinafter mL), 13.9 millimoles (hereinafter mmol)] in tetrahydrofuran (12 mL) at 0° C. under an argon atmosphere was added n-butyllithium (5.8 mL of 2.5M solution, 14.15 mmol), the resulting solution was stirred for 25 minutes (hereinafter min) and then was cooled to −78° C. To this was added a solution of 4-cyano-4-(3-cyclopentyloxy-4-methoxyphenyl)cyclohexan-1-one [2 grams (hereinafter g), 6.64 mmol] in tetrahydrofuran (9 mL). The resulting mixture was stirred at −78° C. for 2 hours (hereinafter h), at which time N-phenyltrifluoromethylsulfonimide (4.98 g, 13.9 mmol) was added. The mixture was allowed to warm slowly to room temperature and after 5 h, the mixture was poured into water and extracted with methylene chloride. The organic extract was dried (potassium carbonate) and concentrated under reduced pressure. The residue was purified by flash chromatography, eluting with 4:1 hexanes/ethyl acetate, to afford an oil (1.09 g, 37%).

Methyl 4-cyano-4-(3-cyclopentyloxy-4-methoxyphenyl)cyclohex-1-ene-1-carboxylate

To a solution of 4-cyano-4-(3-cyclopentyloxy-4-methoxyphenyl)-1-cyclohexenyl trifluoromethylsulfonate (1.0 g, 2.24 mmol) in 1:1 methanol/N,N-dimethylformamide (8 mL) were added methylamine (0.66 ml, 4.72 mmol) and tetrakis(triphenylphosphine)palladium (0.13 g, 011 mmol). The resulting mixture was stirred at room temperature in the dark under a carbon monoxide atmosphere for 3 h. The mixture was partitioned between water and ethyl acetate, the organic extract was washed three times with water, once with brine, was dried (potassium carbonate) and was evaporated. Purification by flash chromatography, eluting with 3:1 hexanes/ethyl acetate, provided an off-white solid (0.64 g, 80%): m.p. 128°–129° C.

Analysis Calc. for $C_{21}H_{25}NO_4 \cdot \frac{1}{8} H_2O$: C 70.52, H 7.12, N 3.92; found: C 70.45, H 6.93, N 3.87.

EXAMPLE 2

4- Cyano-4-(3-cyclopentyloxy-4-methoxyphenyl) cyclohex-1-ene-1-carboxylic acid

To a solution of methyl 4-cyano-4-(3-cyclopentyloxy-4-methoxyphenyl)cyclohex-1-ene-1-carboxylate (0.07 g, 0.18 mmol) in methanol (0.5 mL, containing just enough tetrahydrofuran to solubilize the ester) under an argon atmosphere was added a solution of potassium hydroxide (0.03 g, 0.55 mmol) in water (0.4 mL). The resulting mixture was stirred at room temperature for 4 h, then poured into water and extracted with ethyl acetate. The aqueous phase was acidified with 3N hydrochloric acid and extracted twice with ethyl acetate. The organic phase from the acid extraction was dried (sodium sulfate) and concentrated under reduced pressure to provide a viscous oil, which solidified upon standing. The solid was recrystallized from hexanes/methylene chloride (0.05 g, 82%): m.p. 161°–163° C.

Analysis Calc. for $C_{20}H_{23}NO_4 \cdot \frac{1}{2} H_2O$: C 68.55, H 6.90, N 4.00; found: C 68.65, H 6.55, N 3.82.

EXAMPLE 3

Methyl cis- and trans-[4-cyano-4-(3-cyclopentyloxy-4-methoxyphenyl)cyclohexane-1-carboxylate]

Procedure 3A:

To a solution of methyl 4-cyano-4-(3-cyclopentyloxy-4-methoxyphenyl)cyclohex-1-ene-1-carboxylate (0.26 g, 0.73 mmol) in methanol (12 mL) was added 10% palladium on activated carbon (0.15 g) and the resulting mixture was hydrogenated at 50 psi for 5 h. The mixture was filtered through a pad of Celite and concentrated under reduced pressure. The residue was partitioned between methylene chloride and water, the extract was dried (potassium carbonate) and evaporated to a solid which was primarily the cis-ester (0.14 g, 54%): m.p. 94°–95° C.

Analysis Calc. for $C_{21}H_{27}NO_4 \cdot \frac{1}{8} H_2O$: C 70.32, H 7.38, N 3.90; found: C 70.33, H 7.59, N 3.81.

Procedure 3B:

2-[4-Cyano-4-(3-cyclopentyloxy-4-methoxyphenyl) cyclohexylidene]-1,3-dithiane

To a solution of 2-trimethylsilyl-1,3-dithiane (9.25 mL, 48.7 mmol) in dry tetrahydrofuran (80 mL) at 0° C. under an argon atmosphere was added rapidly n-butyllithium (2.5M in hexanes, 19.2 mL, 48 mmol). After 10 min, the mixture was cooled to −78° C. and a solution of 4- cyano-4-(3-cyclopentyloxy-4-methoxyphenyl)cyclohexan-1-one (7.53 g, 23 mmol) in tetrahydrofuran (40 mL) was added. After 10 min, aqueous sodium chloride was added, the mixture was allowed to warm to room temperature and was diluted with water. This mixture was combined with the product of three substantially similar reactions conducted on ketone (3.04, 6.01 and 6.1 g, 48.3 mmol total), the combined mixture was extracted three times with methylene chloride, the extract was dried (magnesium sulfate) and evaporated. Purification by flash chromatography, eluting with 10% ethyl acetate/hexanes, provided a white solid (26 g, 87%): m.p. 115°–116° C.

Methyl cis-[4-cyano-4-(3-cyclopentyloxy-4-methoxyphenyl)cyclohexane-1-carboxylate]

Perchloric acid (70%, 13.8 mL, 160 mmol) and mercuric chloride (34.1 g, 126 mmol) were added to a solution of 2-[4-cyano-4-(3-cyclopentyloxy-4-methoxyphenyl) cyclohexylidene]-1,3-dithiane (13 g, 31.3 mmol) in methanol (0.5 L) under an argon atmosphere and the mixture was heated at reflux for 2 h and then was allowed to stir at room temperature for 42 h. The mixture was diluted with methylene chloride, was filtered through Celite and the filtrate was combined with that of a similar reaction conducted concurrently on the same scale. The mixture was neutralized with aqueous sodium bicarbonate, was extracted three times with methylene chloride, the organic extract was washed three times with aqueous sodium sulfite, was dried (magnesium sulfate) and was evaporated. Purification by flash chromatography, eluting with 15% ethyl acetate/ hexanes, provided the cis-ester as a white solid (12.4 g, 56%): m.p. 119°–120° C., along with an additional quantity of slightly impure product (2.6 g, 12%).

Methyl trans-[4-cyano-4-(3-cyclopentyloxy-4-methoxyphenyl)cyclohexane-1-carboxylate]

The trans-ester was also isolated from this mixture as a solid (1.04 g, 5%): m.p. 50°–51° C.

Analysis Calc. for $C_{21}H_{27}NO_4 \cdot \frac{3}{4} H_2O$: C 67.99, H 7.74. N 3.78; found: C 67.98, H 7.35, N 3.65.

EXAMPLE 4

Methyl cis- and trans-[4-(3,4-bisdifluoromethoxyphenyl)-4-cyanocyclohexane-1-carboxylate]

Procedure 4A:

2-[4-(3,4-Bisdifluoromethoxyphenyl)-4-cyanocyclohexylidene]-2-tert-butyloxy acetonitrile Sodium hydride (80% dispersion, 0.35 g, 11.7 mmol) was washed three times with pentane, was suspended in tetrahydrofuran (15 mL) at room temperature under an argon atmosphere and diethyl tert-butyl(cyano) methylphosphonate (2.66 g, 10.7 mmol) was added. After 0.5 h, a solution of 4-(3,4-bisdifluoromethoxyphenyl)-4-cyanocyclohexan-1-one (1.77 g. 5.34 mmol) in tetrahydrofuran (5 mL) was added and the mixture was heated at reflux for 0.5 h. The mixture was cooled, aqueous sodium chloride and water were added, the mixture was extracted three times with ether, the extract was dried (magnesium sulfate) and evaporated. Purification by flash chromatography, eluting with 20% ethyl acetate/hexanes, provided the title compound as a white solid (1.18 g, 52%).

Methyl cis- and trans-[4-(3A-bisdifluoromethoxyphenyl)-4-cyanocyclohexane-1-carboxylate]

A mixture of 2-[4-(3,4-bisdifluoromethoxyphenyl)-4-cyanocyclohexylidene]-2-tert-butyloxy acetonitrile (0.25 g, 0.59 mmol) and zinc chloride (0.1 g, 0.7 mmol) in acetic anhydride (1.5 mL) under an argon atmosphere was heated at reflux for 10 min, was cooled, was diluted with water and was extracted three times with ether. The organic extract was washed with water, dried (magnesium sulfate) and evaporated. A solution of this acetate in methanol (6 mL) was treated with a solution of sodium methoxide (25% in methanol, 0.17 mL, 0.71 mmol) and the mixture was stirred under an argon atmosphere for 2 h. The mixture was acidified with hydrochloric acid (1N), water was added and the mixture was extracted three times with methylene chloride. The organic extract was dried (magnesium sulfate) and evaporated. Purification by flash chromatography and eluting with 20% ethyl acetate/hexanes provided the trans-isomer as a colorless oil (0.07 g, 30%).

Analysis Calc. for $C_{17}H_{17}F_4NO_4$: C 54.40, H 4.57, N 3.73; found: C 54.57, H 4.51. N 3.58. The cis-isomer was also isolated as a yellow oil (0.1 g, 47%).

Procedure 4B:

Methyl cis-[4-(3,4-bisdifluoromethoxyphenyl)-4-cyanocyclohexane-1-carboxylate]

A solution of cis-[4-(3,4-bisdifluoromethoxyphenyl)-4-cyanocyclohexane-1-carboxylic acid (EXAMPLE 10, 0.07 g, 0.19 mmol) and trimethylsilyl chloride (0.12 mL, 0.95 mmol) in methanol (5 mL) was stirred at room temperature under an argon atmosphere for 24 h. The solvent was evaporated and the residue was purified by flash chromatography, eluting with 15% ethyl acetate/hexanes, provided a colorless oil (0.05 g, 63%).

Analysis Calc. for $C_{17}H_{17}F_4NO_4$: C 54.40, H 4.57, N 3.73; found: C 54.45, H 4.49, N 3.42.

EXAMPLE 5 cis-[4-Cyano-4-(3-cyclopentyloxy-4-methoxyphenyl)cyclohexane-1-carboxylic acid] and cis-[4-(3,4-bisdifluoromethoxyphenyl)-4-cyanocyclohexane-1-carboxylic acid]

To a solution of methyl cis-[4-cyano-4-(3-cyclopentyloxy-4-methoxyphenyl)cyclohexane-1-carboxylate] (0.12 g, 0.34 mmol) in methanol (0.9 mL, containing just enough tetrahydrofuran to solubilize the ester) under an argon atmosphere was added a solution of potassium hydroxide (0.06 g, 0.9 mmol) in water (0.7 mL). The resulting mixture was stirred at room temperature for 1.5 h, then poured into water and extracted with ethyl acetate. The aqueous phase was acidified with 10% hydrochloric acid and extracted twice with ethyl acetate. The organic phase from the acid extraction was dried (sodium sulfate) and concentrated under reduced pressure to provide a solid. The solid was purified by flash chromatography, eluting with 4% methanol/chloroform, to provide a white solid (0.05 g, 44%): m.p. 157° C.

Analysis Calc. for $C_{20}H_{25}NO_4 \cdot \frac{1}{8} H_2O$: C 68.75, H 7.40, N 4.01; found: C 68.74, H 7.08, N 3.84.

In a similar manner there was prepared:

cis-[4-(3,4-Bisdifluoromethoxyphenyl)-4-cyanocyclohexane-1-carboxylic acid] as a solid: m.p. 143°–144° C.

Analysis Calc. for $C_{16}H_{15}F_4NO_4$: C 53.19, H 4.18, N 3.88; found: C 53.57, H 3.91, N 3.59.

EXAMPLE 6 cis-[4-Cyano-4-(3-cyclopentyloxy-4-methoxyphenyl)cyclohexane-1-carboxylate], tris (hydroxymethyl)ammonium methane salt To a solution of cis-[4-cyano-4-(3-cyclopentyloxy-4-methoxyphenyl)cyclohexane-1-carboxylic acid] (0.17 g, 0.5 mmol) in methanol (2 mL) was added an aqueous solution of tris(hydroxymethyl)aminomethane (1.0M, 0.5 mL). After 10 min, the solvent was evaporated, toluene and methanol were added and the liquids were removed in vacuo. Trituration with ether provided a white solid (0.18 g, 79%): m.p. 191°–194° C.

Analysis Calc. for $C_{24}H_{36}N_2O_7 \cdot 2.5H_2O$: C 56.57, H 8.11, N 5.50; found: C 56.44, H 7.75, N 5.62.

EXAMPLE 7 trans-[4-Cyano-4-(3-cyclopentyloxy-4-methoxyphenyl)cyclohexane-1-carboxylic acid]

To a solution of methyl trans-[4-cyano-4-(3-cyclopentyloxy-4-methoxyphenyl)cyclohexane-1-carboxylate] (0.68 g, 1.9 mmol) in methanol (8 mL, containing just enough tetrahydrofuran to solubilize the ester) under an argon atmosphere was added water (4 mL) and potassium hydroxide (0.32 g, 5.7 mmol). The resulting mixture was stirred at room temperature for 24 h, was acidified with 10% hydrochloric acid and was extracted three times with 10% methanol/methylene chloride. The organic extract was dried (magnesium sulfate) and concentrated under reduced pressure. Purification by flash chromatography, eluting with 4% methanol/methylene chloride, provided a white semi-solid (0.52 g, 80%), which was triturated with ether to yield a white solid (0.43 g): m.p. 157°–158° C.

Analysis Calc. for $C_{20}H_{25}NO_4$: C 69.95, H 7.34, N 4.08; found: C 69.69, H 7.30, N 4.07.

EXAMPLE 8 cis- and trans-[4-Cyano-4-(3-cyclopropylmethoxy-4-methoxyphenyl)cyclohexane-1-carboxylic acid ]

8A. 2-[4-Cyano-4-(3-cyclopentyloxy-4-methoxyphenyl)cyclohexylidene]-2-tert-butyloxy acetonitrile.

This compound, prepared substantially as described above for 2-[4-(3,4-bisdifluoromethoxyphenyl)-4-cyanocyclo-hexylidene]-2-tert-butyloxy acetonitrile in Procedure A of EXAMPLE 4, was isolated as a white solid: m.p. 109°–110° C.

8B. Methyl cis- and trans-[4-cyano-4-(3-hydroxy-4-methoxyphenyl)cyclohexane-1-carboxylate]

These compounds, prepared substantially as described above for methyl cis- and trans-[4-(3,4-bisdifluoromethoxyphenyl)-4-cyanocyclohexane-1-carboxylate] in Procedure A of EXAMPLE 4, were isolated as solids [cis-isomer (0.35 g, 33%): m.p. 105°–106° C.; trans-isomer (0.52 g, 49%): m.p. 103°–104° C.].

8C. Methyl cis-[4-cyano-4-(3-cyclopropylmethoxy-4-methoxyphenyl)cyclohexane-1-carboxyate]

A suspension of methyl cis-[4-cyano-4-(3-hydroxy-4-methoxyphenyl)cyclohexane-1-carboxylate] (0.35 g, 1.20 mmol), powdered potassium carbonate (0.5 g, 3.6 mmol) and bromomethyl cyclopropane (0.35 mL, 3.6 mmol) in dry dimethylformamide (15 mL) under an argon atmosphere was heated at 85° C. for 4 h. The mixture was cooled, was diluted with water and was extracted three times with ether. The organic extract was washed four times with water, once with brine, was dried (potassium carbonate) and was evaporated. Purification by flash chromatography, eluting with 20% ethyl acetate/hexanes, provided an oil (0.34 g, 82%).

8D. cis-[4-Cyano-4-(3-cyclopropylmethoxy-4-methoxyphenyl)cyclohexane-1-carboxylic acid]

The title compound, prepared substantially as described above for cis-[4-cyano-4-(3-cyclopentyloxy-4-methoxyphenyl)cyclohexane-1-carboxylic acid] in EXAMPLE 7, was isolated as a solid: m.p. 165°–167° C.

Analysis Calc. for $C_{19}H_{23}NO_4 \cdot \frac{1}{5} H_2O$: C 68.53, H 7.08, N 4.21; found: C 68.70, H 7.07, N 4.16.

8E. Methyl trans-[4-cyano-4-(3-cyclopropylmethoxy-4-methoxyphenyl)cyclohexane-1-carboxyate]

The title compound, prepared substantially as described above for methyl cis-[4-cyano-4-(3-cyclopropylmethoxy-4- methoxyphenyl)cyclohexane-1-carboxyate]in EXAMPLE 8C was isolated as a solid: m.p. 127.5°–128° C.

Analysis Calc. for $C_{20}H_{25}NO_4 \cdot \frac{3}{8} H_2O$: C 68.60, H 7.41, N 4.00; found: C 68.50, H 7.28, N 3.88.

8F. trans-[4-Cyano-4-(3-cyclopropylmethoxy-4-methoxyphenyl)cyclohexane-1-carboxylic acid]

The title compound, prepared substantially as described above for cis-[4-cyano-4-(3-cyclopentyloxy-4-methoxyphenyl)cyclohexane-1-carboxylic acid] in EXAMPLE 7, was isolated as a solid: m.p. 148° C.

Analysis Calc. for $C_{19}H_{23}NO_4$: C 69.28, H 7.04, N 4.25; found: C 68.97, H 7.03, N 4.25.

EXAMPLE 9 cis- and trans-4-Cyano-4-(3-cyclopropylmethoxy-4difluoromethoxyphenyl)cyclohexane-1-carboxylic acid]

9A. 2-[4-Cyano-4-(3-cyclopropylmethoxy-4-difluoromethoxyphenyl)cyclohexylidene]-1,3-dithiane This compound, prepared substantially as described above for 2-[4-cyano-4-(3-cyclopentyloxy-4-methoxyphenyl) cyclohexylidene]- 1,3-dithiane in Procedure B of EXAMPLE 3, was isolated as a solid: m.p. 84°–85° C.

9B. Methyl cis- and trans-[4-cyano-4-(3-cyclopropylmethoxy-4-difluoromethoxyphenyl) cyclohexane-1-carboxylate]

These compounds, prepared substantially as described above for methyl cis- and trans-[4-cyano-4-(3-cyclopentyloxy-4-methoxyphenyl)cyclohexane-1-carboxylate] in Procedure B of EXAMPLE 3, were isolated as oils.

9C. cis-[4-Cyano-4-(3-cyclopropylmethoxy-4-difluoromethoxyphenyl)cyclohexane-1)carboxylic acid]

This compound, prepared substantially as described above for cis-[4-cyano-4-(3-cyclopentyloxy-4-methoxyphenyl)methoxyphenyl)cyclohexane-1-carboxylic acid] in EXAMPLE 7, was isolated as a solid: m.p. 134°–135° C.

Analysis Calc. for $C_{19}H_{21}F_2NO_4$: C 62.46, H 5.79, N 3.83; found: C 62.15, H 5.83, N 3.88.

9D. trans-[4-Cyano-4-(3-cyclopropylmethoxy-4-difluoromethoxyphenyl)cyclohexane-1-carboxylic acid]

The title compound, prepared substantially as described above for cis-[4-cyano-4-(3-cyclopentyloxy-4-methoxyphenyl)cyclohexane-1-carboxylic acid] in EXAMPLE 7, was isolated as a solid: m.p. 128°–129° C.

EXAMPLE 10 cis-[4-Cyano-4-(3-cyclopentyloxy-4-methoxyphenyl)cyclohexane-1-carboxamide]

To a solution of methyl cis-[4-cyano-4-(3-cyclopentyloxy-4-methoxyphenyl)cyclohexane-1-carboxylate] (0.22 g, 0.62 mmol) and formamide (0.08 mL, 2.08 mmol) at 100° C. in dimethylformamide (2 mL) under an argon atmosphere was added portionwise over 20 min sodium methoxide (25% solution in methanol, 0.1 mL, 0.43 mmol). After an additional 1.25h at 100° C., the mixture was cooled, was poured into isopropanol, was filtered and the filtrate evaporated. The residue was dissolved in ethyl acetate, the organic phase was washed three times with water, was dried (magnesium sulfate) and was concentrated under reduced pressure. Purification by flash chromatography, eluting with 3% methanol/methylene chloride, provided a white foam (0.06 g, 28%).

Analysis Calc. for $C_{20}H_{26}N_2O_3 \cdot \frac{3}{8} H_2O$: C 68.79, H 7.72, N 8.02; found: C 68.86, H 7.49, N 7.93.

EXAMPLE 11 cis-{4-(3,4-Bisdifluoromethoxyphenyl)-4-cyano-1-(3-methyl[1,2,4]oxadiazol-5-yl) cyclohexane} cis-and trans-[4-(3,4-Bisdifluoromethoxyphenyl)-4-cyanocyclohexane-1-carboxamide]

These compounds, prepared substantially as described above for cis-[4-cyano-4-(3-cyclopentyloxy-4-methoxyphenyl)cyclohexane-1-carboxamide] in EXAMPLE 14, were isolated as a solid (cis isomer: m.p. 109°–110° C.) and as an oil (trans isomer).

cis-{4-(3,4-Bisdifluoromethoxyphenyl)-4-cyano-1-(3-methyl[1,2,4]oxadiazol-5-yl)cyclohexane}

A solution of cis-[4-(3,4-bisdifluoromethoxyphenyl)-4-cyanocyclohexane-1-carboxamide] (0.06 g, 0.17 mmol) in N,N-dimethylacetamide dimethyl acetal (0.5 mL) was heated at 110° C. under an argon atmosphere for 1 h, was cooled and the solvent was evaporated. Dioxane (0.35 mL), acetic acid (0.35 mL), hydroxylamine hydrochloride (0.02 g, 0.29 mmol) and 10% aqueous sodium hydroxide (0.09 mL, 0.26 mmol) were added and the mixture was heated at 95° C. under an argon atmosphere for 2.5 h. The mixture was cooled, water was added, the mixture was extracted three times with methylene chloride, the organic extract was dried (magnesium sulfate) and was evaporated. Purification by flash chromatography, eluting with 4% methanol/methylene chloride, provided a solid (0.03 g, 37%). This product was combined with that (0.04 g) from a similar reaction sequence and was triturated with hexane to yield a tan solid: m.p. 83°–84° C.

Analysis Calc. for $C_{18}H_{17}F_4N_3O_3$: C 54.14, H 4.29, N 10.52; found: C 54.11, H 4.35, N 10.13.

EXAMPLE 12 cis-{4-(3,4-Bisdifluoromethoxyphenyl)-4-cyano-1-(2-methyl[1,3,4]oxadiazol-5-yl) cyclohexane} cis-[4-(3,4-Bisdifluoromethoxyphenyl)-4-cyanocyclohexane-1-carbohydrazide]

A solution of methyl cis-[4-(3,4-bisdifluoromethoxyphenyl)-4-cyanocyclohexane-1-carboxylate] (0.2 g, 0.53 mmol) and hydrazine hydrate (0.28 mL, 9.0 mmol) in ethanol (2.5 mL) was heated at reflux for 6 h and then stirred at room temperature for 16 h. Water was added, the mixture was extracted three times with methylene chloride, the extract was dried (magnesium sulfate) and evaporated. Purification by flash chromatography, eluting with 4% methanol/methylene chloride, provided a solid (0.12 g, 58%): m.p. 80°–81° C.

cis-[4-(3,4-Bisdifluoromethoxyphenyl)-4-cyanocyclohexane-1-(2-acetyl-carbohydrazide]

A solution of methyl cis-[4-(3,4-bisdifluoromethoxyphenyl)-4-cyanocyclohexane-1-carbohydrazide] (0.11 g, 0.29 mmol), triethylamine (0.09 mL, 0.65 mmol) and acetic anhydride (0.05 mL, 0.54 mmol) in ethanol (7.5 mL) was heated at reflux for 1 h, was cooled and the solvent was evaporated. Water was added, the mixture was extracted three times with methylene chloride, the extract was dried (magnesium sulfate) and evaporated to provide a white solid (0.11 g, 85%): m.p. 144°–145° C.

cis-{4-(3,4-Bisdifluoromethoxyphenyl)-4-cyano-1-(3-methyl[1,3,4]oxadiazol-5-yl) cyclohexane}

A solution of cis-[4-(3,4-bisdifluoromethoxyphenyl)-4-cyanocyclohexane-1-(2-acetyl-carbohydrazide)] (0.1 g, 0.24 mmol) and phosphorpus oxychloride (0.25 mL, 2.68 mmol) in toluene (3 mL) was heated at reflux under an argon atmosphere for 1.5 h. The mixture was cooled, water was added, the mixture was extracted three times with 5% methanol/methylene chloride, the organic extract was dried (magnesium sulfate) and was evaporated. Purification by flash chromatography, eluting with 1:2 hexanes/ethyl acetate, provided an oil.

Analysis Calc. for $C_{18}H_{17}F_4N_3O_3 \cdot 1.0\ H_2O$: C 51.80, H 4.59, N 10.07; found: C 52.00, H 4.25, N 9.76.

EXAMPLE 13 cis-{4-(3,4-Bisdifluoromethoxyphenyl)-4-cyano-1-(2-methyl[1,3,4]thiadiazol-5-yl) cyclohexane}

A solution of cis-[4-(3,4-bisdifluoromethoxyphenyl)-4-cyanocyclohexane-1-(2-acetyl-carbohydrazide)] (0 1 g, 0.24 mmol) and Lawesson's Reagent (0.13 g, 0.32 mmol) in toluene (3 mL) was heated at reflux under an argon atmosphere for 0.5 h. The mixture was cooled, saturated aqueous sodium bicarbonate was added, the mixture was extracted three times with methylene chloride, the organic extract was dried (magnesium sulfate) and was evaporated. Purification by flash chromatography, eluting with 1:1 hexanes/ethyl acetate, provided a solid: m.p. 66°–67° C.

Analysis Calc. for $C_{18}H_{17}F_4N_3O_2S$: C 52.04, H 4.13, N 10.12; found: C 51.67, H 4.06, N 9.92.

EXAMPLE 14 cis-[4-Cyano-4-(3-cyclopropylmethoxy-4-methoxyphenyl)-1-hydroxy-1-tris(methylthio)methylcyclohexane]

n-Butyllithium (1.9M in hexanes, 0.4 mL, 0.76 mmol) was added dropwise over 5 min to a solution of tris(methylthio)methane (0.11 mL, 0.83 mmol) in dry tetrahydrofuran (3 mL) at −78° C. under an argon atmosphere. After 15 min, a solution of 4-cyano-4-(3-cyclopropylmethoxy-4-methoxyphenyl)cyclohexane (0.2 g, 0.67 mmol) in dry tetrahydrofuran (3 mL) was added dropwise over 10 min. After 0.5 h, aqueous ammonium chloride was added and the mixture was allowed to warm to room temperature. The mixture was extracted three times with methylene chloride, the organic extract was dried (magnesium sulfate) and evaporated. Purification by flash chromatography, eluting with 25% ethyl acetate/hexanes, provided a white solid (0.25 g, 84%): m.p. 123°–124° C.

Analysis Calc. for $C_{22}H_{31}NO_3S_3$: C 58.24, H 6.89, N 3.09; found: C 58.57, H 6.81, N 2.92.

EXAMPLE 15

Methyl cis-[4-cyano-4-(3-cyclopropylmethoxy-4-methoxyphenyl)-1-hydroxycyclohexane-1-carboxylate]

Mercuric chloride (0.23 g, 0.85 mmol) and mercuric oxide (0.08 g, 0.37 mmol) were added to a solution of cis-[4-cyano-4-(3-cyclopropylmethoxy-4-methoxyphenyl)-1-hydroxy-1-tris(methylthio)methylcyclohexane] (0.1 g, 0.22 mmol) in 12:1 methanol/water (2 mL) under an argon atmosphere and the mixture was allowed to stir at room temperature for 4 h. The mixture was filtered through Celite, the filtrate was diluted with water and was extracted three times with methylene chloride, the organic extract was dried (magnesium sulfate) and was evaporated. Purification by flash chromatography, eluting with 35% ethyl acetate/hexanes, provided a sticky solid (0.67 g), which was triturated with ether/hexane to provide a solid (0.47 g, 59%): m.p. 102°–103° C.

Analysis Calc. for $C_{20}H_{25}NO_5 \cdot \frac{1}{2} H_2O$: C 65.20, H 7.11, N 3.80; found: C 65.31, H 6.83, N 3.54.

EXAMPLE 16 cis-[4-Cyano-4-(3-cyclopropylmethoxy-4-methoxyphenyl)-1-hydroxycyclohexane-1-carboxylic acid]

The title compound, prepared substantially as described above for cis-[4-cyano-4-(3-cyclopentyloxy-4-methoxyphenyl)cyclohexane-1-carboxylic acid] in EXAMPLE 5, was isolated as a solid: m.p. 168°–169° C.

Analysis Calc. for $C_{19}H_{23}NO_5 \cdot \frac{1}{4} H_2O$: C 65.22, H 6.77, N 4.00: found: C 64.94, H 6.62, N 3.80.

EXAMPLE 17 cis-[4-Cyano-4-(3-cyclopropylmethoxy-4-methoxyphenyl)-1-hydroxycyclohexane-1-carboxamide]

A solution of cis-[4-cyano-4-(3-cyclopropylmethoxy-4-methoxy-phenyl)-1-hydroxycyclohexane-1-carboxylic acid] (0.15 g, 0.42 mmol) and a trace of sodium cyanide in methanol (1.5 mL) contained in a pressure vessel was cooled to −78° and anhydrous ammonia (2 mL) was condensed into the tube. The tube was sealed, was allowed to come to room temperature and the reaction was stirred for 2 days. The ammonia was allowed to evaporate and the reaction was partitioned between water and methylene chloride. The organic extract was dried (magnesium sulfate) and the solvent was evaporated. Purification by flash chromatography, eluting with 3% methanol/chloroform, provided a solid (0.054 g, 38%): m.p. 144°–145° C.

Analysis Calc. for $C_{19}H_{24}N_2O_4 \cdot \frac{1}{4} H_2O$: C 65.41, H 7.08, N 8.03; found: C 65.16, H 6.96, N 7.86.

EXAMPLE 18

Methyl cis-[4-cyano-4-(3-cyclopropylmethoxy-4-methoxyphenyl)-1-methoxycyclohexane-1-carboxylate]

Silver (I) oxide (0.62 g, 2.7 mmol) was added to a solution of methyl cis-[4-cyano-4-(3-cyclopropylmethoxy-4-methoxyphenyl)-1-hydroxycyclohexane-1-carboxylate] (0.62 g, 1.7 mmol) and iodomethane (5 mL) in acetonitrile (5 mL) under an argon atmosphere and the mixture was heated at reflux in the dark for 18 h. The mixture was cooled, was filtered through Celite and the filtrate was evaporated. Purification by flash chromatography, eluting with 20% ethyl acetate/hexanes, provided a solid (0.55 g, 86%): m.p. 75°–76° C.

Analysis Calc. for $C_{21}H_{27}NO_5$: C 67.54, H 7.29, N 3.75; found: C 67.46, H 7.30, N 3.80.

EXAMPLE 19 cis-[4-Cyano-4-(3-cyclopropylmethoxy-4-methoxyphenyl)-1-methoxycyclohexane-1-carboxylic acid]

The title compound, prepared substantially as described above for cis-[4-cyano-4-(3-cyclopentyloxy-4-methoxyphenyl)cyclohexane-1-carboxylic acid] in EXAMPLE 5, was isolated as a solid: m.p. 110°–112° C.

Analysis Calc. for $C_{20}H_{25}NO_5$: C 66.84, H 7.01, N 3.90; found: C 66.64, H 7.29, N 3.95.

EXAMPLE 20 cis-[4-Cyano-4-(3-cyclopropylmethoxy-4-methoxyphenyl)-1-methoxycyclohexane-1-carboxamide]

A solution of cis-[4-cyano-4(3-cyclopropylmethoxy-4-methoxyphenyl)-1-methoxycyclohexane-1-carboxylic acid] (0.13 g, 0.36 mmol) and N-methylmorpholine (0.05 mL, 0.45 mmol) in 1,2-dimethoxyethane (2.5 mL) at room temperature under an argon atmosphere was treated with isobutyl chloroformate (0.05 mL, 0.39 mmol). After 10 min, concentrated ammonium hydroxide (6 drops) was added and the mixture was stirred for an additional 0.5 h. Water was added, the mixture was extracted three times with 5% methanol/methylene chloride, the organic extract was dried (magnesium sulfate) and the solvent was evaporated. Purification by flash chromatography, eluting with 3% methanol/chloroform, provided a solid (0.13 g, 100%): m.p. 165°–166° C.

Analysis Calc. for $C_{20}H_{26}N_2O_4 \cdot \frac{3}{8} H_2O$: C 65.78, H 7.35, N 7.67; found: C 65.65, H 7.23, N 7.47.

EXAMPLE 21

Methyl trans-[4-cyano-4-(3-cyclopropylmethoxy-4-methoxyphenyl)-1-hydroxycyclohexane-1-carboxylate]

trans-[4-Cyano-4-(3-cyclopropylmethoxy-4-methoxyphenyl)-1-cyclohexane-1,1-diyl]oxirane]

To a mixture of 80% sodium hydride in mineral oil (0.33 g, 11 mmol) and trimethylsulfoxonium iodide (1.69 g, 7.67 mmol) at room temperature under an argon atmosphere was added dropwise dimethylsulfoxide (12 mL) and the reaction mixture was stirred for 30 min. A solution of 4cyano-4-(3-cyclopropylmethoxy-3-methoxyphenyl)cyclohexanone (2.00 g, 6.68 mmol) in dimethylsulfoxide (5 mL) was added and stirring was continued for 30 min. The reaction mixture was quenched with saturated ammonium chloride, was partitioned between ethyl acetate and water, was dried (magnesium sulfate) and the solvent was removed in vacuo. The residue was purified by flash chromatography, eluting with 1:3 ethyl acetate/hexanes, to provide a colorless oil (1.42 g, 68%). Analysis Calc. for $C_{19}H_{23}NO_3 \cdot H_2O$: C 68.86, H 7.30, N 4.23; found: C 69.22, H 7.11, N 4.17. Starting material was also recovered (0.6 g, 30%).

trans-[4-Cyano-4-(3-cyclopropylmethoxy-4-methoxyphenyl)-1-hydroxymethyl-1-cyclohexanol]

A mixture of trans-4-cyano-4-(3-cyclopropylmethoxy-4-methoxyphenyl)cyclohexane-1-methyleneoxide (1.31 g, 4.18 mmol) and potassium hydroxide (0.14 g, 2.5 mmol) in 85:15 dimethylsulfoxide/water (140 mL) under an argon atmosphere was heated at 100–110° C. for 1 h, was cooled, was diluted with water and was extracted three times with ethyl acetate. The organic extract was washed five times with water, was dried (magnesium sulfate) and was evaporated. Purification by flash chromatography, eluting with 3.5:96.5 methanol/dichloromethane, provided the trans-isomer as a sticky white solid: m.p. 38°–42° C (0.96 g, 69%).

Analysis Calc. for $C_{19}H_{25}NO_4$: C 68.86, H 7.60, N 4.23; found: C 68.96, H 7.62, N 4.03.

trans-[4-Cyano-4-(3- cyclopropylmethoxy-4-methoxyphenyl)-1-hydroxycyclohexane-1-carboxaldehyde]

To a solution of oxalyl chloride (0.28 mL, 3.21 mmol) in dichloromethane (3.5 mL) at –78° C. under an argon atmosphere was added dropwise a solution of dimethylsulfoxide (0.46 mL, 6.48 mmol) in dichloromethane (3.5 mL) such that the internal temperature did not exceed –60° C. A solution of trans-4-cyano-4-(3-cyclopropylmethoxy-3-methoxyphenyl)-1-hydroxymethyl-1-cyclohexanol (0.89 g, 2.68 mmol) in dichloromethane (7 mL) was added dropwise and stirring was continued for 30 min. Triethylamine (1.80 mL, 12.9 mmol) was added over 10 min, then 5 min later, the reaction mixture was allowed to warm to room temperature over 1 h. The reaction mixture was quenched with water and was extracted with three portions of dichloromethane. The combined organic layers were washed with 1% hydrochloric acid, 5% sodium carbonate and water, dried (magnesium sulfate) and the solvent was removed in vacuo to provide crude aldehyde (0.85 g, 97%).

Methyl trans-[4cyano-4-(3-cyclopropylmethoxy-4-methoxyphenyl)-1-hydroxycyclohexane-1-carboxylate]

To a solution of trans-[4-cyano-4-(3-cyclopropylmethoxy-4-methoxyphenyl)-1-hydroxycyclohexane-1-carboxaldehyde (0.79 g, 2.4 mm01) in methanol (25 mL) at 0° C. under an argon atmosphere was rapidly added a solution of potassium hydroxide (0.36 g, 6.43 mmol) in methanol (5 mL), followed by a solution of iodine (0.80 g, 3.15 mmol) in methanol (5 mL). After 15 min the reaction was acidified with 1N hydrochloric acid and extracted with three portions of dichloromethane. The combined organic layers were washed with aqueous sodium bisulfite until color was discharged, then with water, dried (magnesium sulfate), and the solvent was removed in vacuo. Purification by flash chromatography, eluted with 35:65 ethyl acetate/hexanes, provided a white solid (0.82 g, 94%): m.p.148°–149° C.

Analysis Calc. for $C_{20}H_{25}NO_5 \cdot \frac{1}{4} H_2O$: C 66.0, H 7.06, N 3.84; found: C 65.86, H 6.92, N 3.85.

EXAMPLE 22 trans-[4-Cyano-4-(3-cyclopropylmethoxy-4-methoxyphenyl)-1-hydroxycyclohexane-1-carboxylic acid]

The title compound, prepared substantially as described above for cis-[4-cyano-4-(3-cyclopentyloxy-4- methoxyphenyl)cyclohexane-1-carboxylic acid] in EXAMPLE 5, was isolated as a solid: m.p. 147°–148° C.

Analysis Calc. for $C_{19}H_{23}NO_5$: C 66.07, H 6.71, N 4.06; found: C 66.02, H 6.71, N 4.04.

EXAMPLE 23

Methyl trans-[4-cyano-4-(3-cyclopropylmethoxy-4-methoxyphenyl)-1-methoxycyclohexane-1-carboxylate]

The title compound, prepared substantially as described above for methyl cis-[4-cyano-4-(3-cyclopropylmethoxy-4-methoxyphenyl) 1-methoxycyclohexane-1-carboxylate]in EXAMPLE 18, was isolated as a solid: m.p. 84°–85° C.

Analysis Calc. for $C_{21}H_{27}NO_5$: C 67.54, H 7.29, N 3.75; found: C 67.34, H 7.25, N 3.77.

EXAMPLE 24 trans-[4- Cyano-4-(3-cyclopropylmethoxy-4-methoxyphenyl)-1-methoxycyclohexane-1-carboxylic acid]

The title compound, prepared substantially as described above for cis-[4-cyano-4-(3-cyclopentyloxy-4methoxyphenyl)cyclohexane-1-carboxylic acid] in EXAMPLE 5, was isolated as a solid: m.p. 158°–159° C.

Analysis Calc. for $C_{20}H_{25}NO_5 \cdot \frac{1}{4} H_2O$: C 66.01, H 7.06, N 3.85; found: C 65.98, H 6.91, N 3.75.

EXAMPLE 25 trans-[4-Cyano-4-(3-cyclopropylmethoxy-4-methoxyphenyl)-1-methoxycyclohexane-1-carboxamide]

The title compound, prepared substantially as described above for cis-[4-cyano-4-(3-cyclopentyloxy-4-methoxyphenyl)-1-methoxycyclohexane-1-carboxamide] in EXAMPLE 20, was isolated as a solid: m.p. 168°–169° C.

Analysis Calc. for $C_{20}H_{26}N_2O_4 \cdot \frac{1}{8} H_2O$: C 66.60, H 7.34, N 7.70; found: C 66.60, H 7.30, N 7.74.

EXAMPLE 26 cis-[4-Cyano-4-(3-cyclopentyloxy-4-methoxyphenyl)cyclohexane-1-carboxamic acid]

The title compound, prepared substantially as described above for cis-[4-cyano-4-(3-cyclopentyloxy-4-methoxyphenyl)-1-methoxycyclohexane-1-carboxamide] in EXAMPLE 20 but using hydroxylmine instead of ammonia, was isolated as a solid: m.p. 100°–102° C.

Analysis Calc. for $C_{20}H_{26}N_2O_4$: C 67.02, H 7.31, N 7.82; found: C 66.75, H 7.58, N 7.42.

EXAMPLE 27

N-Methyl-cis-[4-cyano-4-(3-cyclopentyloxy-4-methoxyphenyl)cyclohexane-1-carboxamic acid]

The title compound, prepared substantially as described above for cis-[4-cyano-4-(3-cyclopentyloxy-4-methoxyphenyl)-1-methoxycyclohexane-1-carboxamide] in EXAMPLE 20 but using N-methylhydroxylamine instead of ammonia, was isolated as a solid: m.p. 75°–76° C.

Analysis Calc. for $C_{21}H_{28}N_2O_4 \cdot \frac{1}{4} H_2O$: C 66.91, H 7.62, N 7.43: found: C 66.95, H 7.54, N 7.35.

EXAMPLE 28 cis-[4-Cyano-4-(3-cyclopentyloxy-4-methoxyphenyl)cyclohexane-1-N-(2-cyanoethyl) carboxamide]

To a solution of cis-[4-cyano-4-(3-cyclopentyloxy-4-methoxyphenyl)cyclohexane-1-carboxylic acid] (0.55 g, 1.6 mmol), 1-hydroxybenzotriazole (0.24 g, 1.76 mmol) and 3-aminopropionitrile (0.11 g, 1.6 mmol) in dichloromethane (10 mL) at 0° C. under an argon atmosphere was added 1-(3-diethylaminopropyl)-3-ethylcarbodiimide hydrochloride (0.34 g, 1.76 mmol) and the mixture was allowed to warm to room temperature. After 6 h, the mixture was diluted with dichloromethane, was washed twice with 10% aqueous potassium carbonate, twice with 10 % hydrochloric acid and was dried (magnesium sulfate). The solvent was evaporated and the residue was crystallized from hexanes/ ethyl acetate to provide a solid (0.54 g, 85%): m.p. 146°–147° C.

Analysis Calc. for $C_{23}H_{29}N_3O_3$: C 69.85, H 7.39, N 10.62; found: C 69.49 H 7.41, N 10.46.

EXAMPLE 29 cis-[1-(2-Cyanoethyl)-5-{4-cyano-4-(3-cyclopentyloxy-4-methoxyphenyl) cyclohexyl}tetrazole]

To a solution of cis-[4-cyano-4-(3-cyclopentyloxy-4-methoxyphenyl)cyclohexane-1-N-(2-cyanoethyl) carboxamide] (0.15 g, 0.37 mmol), triphenylphosphine (0.19 g, 0.73 mmol) and trimethylsilylazide (0.097 mL, 0.73 mmol) in dry tetrahydrofuran (2 mL) at room temperature under an argon atmosphere was added dropwise diethyl azodicarboxylate (0.12 mL, 0.73 mmol) and the mixture was stirred in the dark for 24 h. Ceric ammonium nitrate (0.81 g, 1.48 mmol) in water (10 mL) was added at 0° C., the mixture was extracted three times with dichloromethane, the extract was dried (magnesium sulfate) and the solvent was evaporated. Purification by flash chromatography, eluting with 2:1 ethyl acetate/hexanes, followed by recrystallization from hexanes/ethyl acetate, provided a white solid (0.03 g, 19%): m.p. 149°–150° C.

Analysis Calc. for $C_{23}H_{28}N_6O_2$: C 65.69, H 6.71, N 19.99; found: C 65.45 H 6.72. N 19.91.

EXAMPLE 30 cis-[4-Cyano-4-(3-cyclopentyloxy-4-methoxyphenyl)-1-(5-tetrazolyl)cyclohexane]

A mixture of cis-[1-(2-cyanoethyl)-5-{4-Cyano-4-(3-cyclopentyloxy-4-methoxyphenyl)cyclohexyl}tetrazole] (0.098 g, 0.23 mmol) and sodium hydroxide (0.018 g, 0.46 mmol) in 10:1 tetrahydrofuran/water (5 mL) at room temperature under an argon atmosphere was stirred overnight. The mixture was acidified with 3N hydrochloric acid, was extracted three times with ethyl acetate, the extract was dried (magnesium sulfate) and the solvent was evaporated. Purification by flash chromatography, eluting with 80:20:2 chloroform/methanol/water, followed by trituration with hexanes/ethyl acetate, provided a white solid (0.038 g, 45%): m.p. 190°–191° C.

Analysis Calc. for $C_{20}H_{25}N_5O_2 \cdot \frac{1}{2} H_2O$: C 63.81, H 6.96, N 18.60; found: C 64.07 H 6.79, N 18.54.

METHODS OF TREATMENT

In order to use a compound of Formula (I) or a pharmaceutically acceptable salt thereof for the treatment of humans and other mammals, it is normally formulated in accordance with standard pharmaceutical practice as a pharmaceutical composition. The compounds of Formula (I) or a pharmaceutically acceptable salt thereof can be used in the manufacture of a medicament for the prophylatic or therapeutic treatment of any disease state in a human or other mammal which is mediated by inhibition of PDE IV, such as but not limited to asthma, allergic, or inflammatory diseases. The compounds of Formula (I) are administered in an amount sufficient to treat such a disease in a human or other mammal.

The method of treatment and monitoring for an HIV-infected human manifesting immune dysfunction or cytokine-mediated disease associated problems is taught in Hanna, WO 90/15534, Dec. 27, 1990. In general, an initial treatment regimen can be copied from that known to be effective in interfering with TNF activity for other TNF mediated disease states by the compounds of Formula (I). Treated individuals will be regularly checked for T cell numbers and T4/T8 ratios and/or measures of viremia such as levels of reverse transcriptase or viral proteins, and/or for profession of monokine-mediated disease associated problems such as cachexia or muscle degeneration. If no effect is seen following the normal treatment regimen, then the amount of the monokine activity interfering agent administered is increased, e.g., by fifty percent per week.

The pharmaceutical composition of the present invention will comprise an effective, non-toxic amount of a compound of Formula (I) and a pharmaceutically acceptable career or diluent. The compounds of Formula (I) are administered in conventional dosage forms prepared by combining a compound of Formula (I) in an amount sufficient to produce TNF production inhibiting activity, respectively, with standard pharmaceutical carriers according to conventional procedures. These procedures may involve mixing, granulating, and compressing or dissolving the ingredients as appropriate to the desired preparation.

Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 gram. When a liquid carrier is used, the preparation will be in the form of a syrup, emulsion, soft gelatin capsule, sterile injectable liquid such as an ampule or nonaqueous liquid suspension. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates, or oils and are incorporated in a soft gelatin capsule shell. A syrup formulation will generally consist of a suspension or solution of the compound or salt in a liquid career for example, ethanol, glycerine, or water with a flavoring or coloring agent.

The daily dosage regimen for oral administration is suitably about 0.001 mg/kg to 100 mg/kg, preferably 0.01 mg/Kg to 40 mg/Kg, of a compound of Formula (I) or a pharmaceutically acceptable salt thereof calculated as the free base. The active ingredient may be administered from 1 to 6 times a day, sufficient to exhibit activity.

While it is possible for an active ingredient to be administered neat, it is preferable to present it as a pharmaceutical formulation. The active ingredient may comprise, for topical administration, from 0.001% to 10% w/w, e.g., from 1% to 2% by weight of formulation, although it may comprise as much as 10% w/w but preferably not in excess of 5% w/w and more preferably from 0.1% to 1% w/w of Formulation.

Formulations of the present invention comprise an active ingredient together with one or more acceptable carrier(s) thereof and optionally any other therapeutic ingredient(s). The carrier(s) must be 'acceptable' in the sense of being compatible with the other ingredients of Formulation and not deleterious to the recipient thereof.

It will be recognized by one of skill in the art that the form and character of the pharmaceutically acceptable career or diluent is dictated by the amount of active ingredient with which it is to be combined, the route of administration, and other well-known variables.

No toxic effects are expected when these compounds are administered in accordance with the present invention.

Utility Examples

Example A

Inhibitory effect of compounds of the Formula (I) on in vitro TNF production by human monocytes The inhibitory effect of compounds of the Formula (I) on in vitro TNF production by human monocytes may be determined by the protocol as described in Badger et al., EPO published Application 0 411 754 A2, Feb. 6, 1991, and in Hanna, WO 90/15534, Dec. 27, 1990.

Example B

Two models of endotoxic shock have been utilized to determine in vivo TNF activity for the compounds of the Formula (I). The protocol used in these models is described in Badger et al., EPO published Application 0 411 754 A2, Feb. 6, 1991, and in Hanna, WO 90/15534, Dec. 27, 1990.

The exemplified compounds herein demonstrated a positive in vivo response in reducing serum levels of TNF induced by the injection of endotoxin.

Example C

Isolation of PDE Isozymes

The phosphodiesterase inhibitory activity and selectivity of the compounds of the Formula (I) can be determined using a battery of five distinct PDE isozymes. The tissues used as sources of the different isozymes are as follows: 1) POE Ib, porcine aorta; 2) PDE Ic, guinea-pig heart; 3) PDE III, guinea-pig heart; 4) PDE IV, human monocyte; and 5) PDE V (also called "Ia"), canine tracheaolis. PDEs Ia, Ib, Ic and III are partially purified using standard chromatographic techniques [Torphy and Cieslinski, Mol. Pharmacol., 37:206–214, 1990]. PDE IV is purified to kinetic homogeneity by the sequential use of anion-exchange followed by heparin-Sepharose chromatography [Torphy et al., J. Biol. Chem., 267:1798–1804, 1992].

Phosphodiesterase activity is assayed as described in the protocol of Torphy and Cieslinski, Mol. Pharmacol., 37:206–214, 1990. Positive $IC_{50}$'s in the nanomolar to µM range for compounds of the workings examples described herein for Formula (I) have been demonstrated.

Example D

The ability of selected PDE IV inhibitors to increase cAMP accumulation in intact tissues is assessed using U-937 cells, a human monocyte cell line that has been shown to contain a large amount of PDE IV. To assess the activity of PDE IV inhibition in intact cells, nondifferentiated U-937 cells (approximately $10^5$ cells/reaction tube) were incubated with various concentrations (0.01–1000 μM) of PDE inhibitors for one minute and 1 μM prostaglandin E2 for an additional four minutes. Five minutes after initiating the reaction, cells were lysed by the addition of 17.5% perchloric acid, the pH was neutralized by the addition of 1M potassium carbonate and cAMP content was assessed by RIA. A general protocol for this assay is described in Brooker et al., Radioimmunoassay of cyclic AMP and cyclic GMP., Adv. Cyclic Nucleotide Res., 10:1–33, 1979. The compounds of the working examples as described herein for Formula (I) have demonstrated a positive $EC_{50}s$ in the μM range in the above assay.

What is claimed is:

1. A compound of Formula (I):

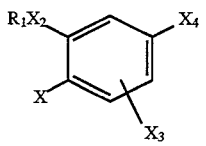

wherein:

$R_1$ is $—(CR_4R_5)_nC(O)O(CR_4R_5)_mR_6$, $—(CR_4R_5)_nC(O)NR_4(CR_4R_5)_mR_6$, $—(CR_4R_5)_nO(CR_4R_5)_mR_6$, or $—(CR_4R_5)_rR_6$ wherein the alkyl moieties may be optionally substituted with one or more halogens;

m is 0 to 2;

n is 1 to 4;

r is 0 to 6;

$R_4$ and $R_5$ are independently selected from hydrogen or a $C_{1-2}$ alkyl;

$R_6$ is hydrogen, methyl, hydroxyl, aryl, halo substituted aryl, aryloxy $C_{1-3}$ alkyl, halo substituted aryloxy $C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group; provided that:

a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in $—(CR_4R_5)^NO(CR_4R_5)_mR_6$;

X is $YR_2$, halogen, nitro, $NR_4R_5$, or formyl amine;

Y is O or $S(O)_{m'}$;

m' is 0, 1, or 2;

$X_2$ is O or $NR_8$;

$X_3$ is hydrogen or X;

$X_4$ is

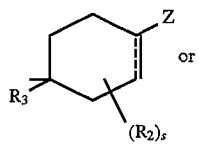

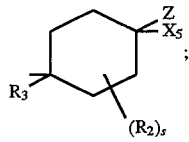

$X_5$ is H, $R_9$, $OR_8$, CN, $C(O)R_8$, $C(O)OR_8$, $C(O)NR_8R_8$, or $NR_8R_8$;

$R_2$ is independently selected from the group consisting of $—CH_3$ and $—CH_2CH_3$ optionally substituted by 1 or more halogens;

s is 0 to 4;

$R_3$ is cyclopropyl optionally substituted by $R_8'$,

Z is $C(Y')R_{14}$, $C(O)OR_{14}$, $C(Y')NR_{10}R_{14}$, $C(NR_{10})NR_{10}R_{14}$, CN, $C(NOR_8)R_{14}$, $C(O)NR_8NR_8C(O)R_8$, $C(O)NR_8NR_{10}R_{14}$, $C(NOR_{14})R_8$, $C(NR_8)NR_{10}R_{14}$, $C(NR_{14})NR_8R_8C(NCN)NR_{10}R_{14}$, $C(NCN)SR_9$, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2oxadiazolyl [1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl); wherein all of the heterocylic ring systems may be optionally substituted one or more times by $R_{14}$;

the dotted line in formula (a) represents a single or double bond;

Y' is O or S;

$R_7$ is $—(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, —F, —Br, —Cl, $—NO_2$, $—NR_{10}R_{11}$, $—C(O)R_8$, $—C(O)OR_8$, $—OR_8$, —CN, $—C(O)NR_{10}R_{11}$, $—OC(O)NR_{10}R_{11}$, $—OC(O)R_8$, $—NR_{10}C(O)NR_{10}R_{11}$, $—NR_{10}C(O)R_{11}$, $—NR_{10}C(O)OR_9$, $—NR_{10}C(O)R_{13}$, $—C(NR_{10})NR_{10}R_{11}$, $—C(NCN)NR_{10}R_{11}$, $—C(NCN)SR_9$, $—NR_{10}C(NCN)SR_9$, $—NR_{10}C(NCN)NR_{10}R_{11}$, $—NR_{10}S(O)_2R_9$, $—S(O)_mR_9$, $—NR_{10}C(O)C(O)NR_{10}R_{11}$, $—NR_{10}C(O)C(O)R_{10}$, thiazolyl, imidazolyl, oxazolyl, pyrazolyl, triazolyl, or tetrazolyl;

q is 0, 1, or 2;

$R_{12}$ is $C_3$–$C_7$-cycloalkyl, (2-, 3- or 4-pyridyl), pyrimidyl, pyrazolyl, (1- or 2-imidazolyl), thiazolyl, triazolyl, pyrrolyl, piperazinyl, piperidinyl, morpholinyl, furanyl, (2- or 3-thienyl), (4- or 5-thiazolyl), quinolinyl, naphthyl, or phenyl;

$R_8$ is independently selected from hydrogen or $R_9$;

$R_8'$ is $R_8$ or fluorine;

$R_9$ is $C_{1-4}$ alkyl optionally substituted by one to three fluorines;

$R_{10}$ is $OR_8$ or $R_{11}$;

$R_{11}$ is hydrogen, or $C_{1-4}$ alkyl optionally substituted by one to three fluorines; or when $R_{10}$ and $R_{11}$ are as $NR_{10}R_{11}$ they may together with the nitrogen form a 5 to 7 membered ring optionally containing at least one additional heteroatom selected from O/N/or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_{10}$ and $R_{14}$ are as $NR_{10}R_{14}$ they may together with the nitrogen form a 5 to 7 membered ring optionally containing one or more additional heteroatoms selected from O, N, or S;

provided that:

f) when $R_{12}$ is N-pyrazolyl, N-imidazolyl, N-triazolyl, N-pyrrolyl, N-piperazinyl, N-piperidinyl, or N-morpholinyl, then q is not 1; or or the pharmaceutically acceptable salts thereof.

2. A pharmaceutical composition comprising a compound of Formula (I) according to claim 1 and a pharmaceutically acceptable excipient.

3. A method for treating an allergic or inflammatory disease which method comprises administering to a subject in need thereof an effective amount of a compound of Formula (I) according to claim 1 alone or in combination with a pharmaceutically acceptable excipient.

* * * * *